(12) United States Patent
Chiba et al.

(10) Patent No.: US 11,058,685 B2
(45) Date of Patent: Jul. 13, 2021

(54) THERAPEUTIC AGENT FOR TUMORS IDENTIFIED BY PHOSPHORYLATION OF PROTO-ONCOGENE PROTEIN BELONGING TO VAV FAMILY

(71) Applicant: University of Tsukuba, Ibaraki (JP)

(72) Inventors: Shigeru Chiba, Ibaraki (JP); Mamiko Yanagimoto, Ibaraki (JP)

(73) Assignee: UNIVERSITY OF TSUKUBA, Tsukuba (JP)

( * ) Notice: Subject to any disclaimer, the term of this patent is extended or adjusted under 35 U.S.C. 154(b) by 0 days.

(21) Appl. No.: 16/393,138

(22) Filed: Apr. 24, 2019

(65) Prior Publication Data
US 2020/0069684 A1 Mar. 5, 2020

Related U.S. Application Data

(63) Continuation of application No. PCT/JP2017/038595, filed on Oct. 19, 2017.

(30) Foreign Application Priority Data

Nov. 2, 2016 (JP) .............................. JP2016-215521

(51) Int. Cl.
*A61K 31/506* (2006.01)
*G01N 33/574* (2006.01)

(52) U.S. Cl.
CPC ....... *A61K 31/506* (2013.01); *G01N 33/5748* (2013.01)

(58) Field of Classification Search
CPC .................................................. A61K 31/506
USPC .................................................. 514/252.19
See application file for complete search history.

(56) References Cited

PUBLICATIONS

Chang et al., "VAV3 is Required for P190-BCR-ABL-Induced Lymphoid Progenitor Transformation and Leukemogenesis", Experimental Hematology, 2011, vol. 39, Suppl. 1, S. 39, Abstract No. 01115186.
Feldman et al., "Recurrent rearrangements of the VAV1 gene in peripheral T-cell lymphomas", Laboratory Investigation, 2015, vol. 95, Suppl. 1, p. 344A, Abstract No. 1375, entire text.
Guo et al., "Novel Fusion Transcripts Identified in Angioimmunoblastic T Cell Lymphoma", Laboratory Investigation, 2013, vol. 93, Suppl. 1, p. 330A, Abstract No. 1383, entire text.
Hacken et al., "Targeting the LYN/HS1 signaling axis in chronic lymphocytic leukemia", Blood, 2013, vol. 121, No. 12, pp. 2264-2273, p. 2268, lower left column, line 6 to right column, line 6, p. 2269, right column, lines 15-30, Total 11 pages.
Hassold et al., "Enhancement of natural killer cell effector functions against selected lymphoma and leukemia cell lines by dasatinib", International Journal of Cancer, 2012, vol. 131, pp. E916-E927.

International Preliminary Examination Report (PCT/IPEA/409 and PCT/IPEA/416), issued in PCT/JP2017/038595, dated Nov. 26, 2018.
International Search Report (PCT/ISA/210) issued in PCT/JP2017/038595, dated Jan. 23, 2018.
Lewis-Tuffin et al., "Src family kinases differentially influence glioma growth and motility", Molecular Oncology, 2015, vol. 9, pp. 1783-1798, abstract, pp. 1787-1790 "Results 3.1" column, p. 1793, left column, lines 20-22, fig. 1, 3B, C.
Michels et al., "SRC Signaling is Crucial in the Grouth of Synovial Sarcoma Cells", Cancer Research, 2013, vol. 73, No. 8, pp. 2518-2528, Total 13 pages.
Palomero et al., "Recurrent mutations in epigenetic regulators, RHOA and FYN kinase in peripheral T cell lymphomas", nature genetics, 2017, vol. 46, No. 2, pp. 166-170, in particular, abstract, Total 8 pages.
Sakata-Yanagimoto et al., "Somatic RHOA mutation in angioimmunoblastic T cell lymphoma", Nature Genetics, Feb. 2014, vol. 46, No. 2, pp. 171-175, Total 8 pages.
Shah et al., "Overriding imatinib resistance with a novel ABL kinase inhibitor", Science 2004, vol. 305, pp. 399-401, Total 4 pages.
Talpaz et al., "Dasatinib in Imatinib-Resistant Philadelphia Chromosome-Positive Leukemias", The New England Journal of Medicine, Jun. 15, 2000, vol. 354, No. 24, pp. 2531-2541.
Timpson et al., "Spatial Regulation of RhoA Activity during Pancreatic Cancer Cell Invasion Driven by Mutant p53", Cancer Research, 2011, vol. 71, No. 3, pp. 747-757, p. 753, lower right column, line 3 to p. 755, lower left column, line 5, Total 12 pages.
Written Opinion (PCT/ISA/237) issued in PCT/JP2017/038595, dated Jan. 23, 2018.
Written Opinion of the International Preliminary Examining Authority for PCT/JP2017/038595 (PCT/IPEA/408) dated Aug. 14, 2018.
Dunn et al., "Dasatinib sensitizes KRAS mutant colorectal tumors to cetuximab", Oncogene, 2011, vol. 30, pp. 561-574 (14 pages).
Eustace et al., "Predictive biomarkers for dasatinib treatment in melanoma", Oncoscience, 2014 (published online Mar. 12, 2014), vol. 1, No. 2, pp. 158-166 (9 pages).
Extended European Search Report, dated Sep. 18, 2020, for European Application No. 17866638.4.
Lopez-Acevedo et al, "Dasatinib (BMS-35482) potentiates the activity of gemcitabine and docetaxel in uterine leiomyosarcoma cell lines", Gynecologic Oncology Research and Practice, 2014, vol. 1, No. 2, pp. 1-10 (10 pages).
Nehoff, "A combination of tyrosine kinase inhibitors, crizotinib and dasatinib for the treatment of glioblastoma multiforme", Oncotarget, 2015 (published online Oct. 16, 2015), vol. 6, No. 35, pp. 37948-37964 ( 17 pages).

(Continued)

*Primary Examiner* — Kevin E Weddington
(74) *Attorney, Agent, or Firm* — Birch, Stewart, Kolasch & Birch, LLP

(57) ABSTRACT

The present invention provides a therapeutic agent and others for various tumors including angioimmunoblastic T-cell lymphoma (AITL), which is an orphan disease. The present invention relates to a therapeutic agent and others for tumors identified by phosphorylation of a proto-oncogene protein belonging to the VAV family, which comprises dasatinib or a prodrug thereof or a pharmacologically acceptable salt thereof or a hydrate or solvate thereof as an active ingredient.

9 Claims, 17 Drawing Sheets
(10 of 17 Drawing Sheet(s) Filed in Color)
Specification includes a Sequence Listing.

(56) References Cited

PUBLICATIONS

Shi et al., "Synergistic antitumor effects of dasatinib and oxaliplatin in gastric cancer cells", Cancer Chemother Pharmacol, 2013 (published online May 28, 2013), vol. 72, pp. 35-44 (10 pages).

Fujisawa et al., "Activation of RHOA-VAV1 signaling in angioimmunoblastic T-cell lymphoma", Leukumia, 2018, vol. 32, pp. 694-702 (9 pages).

Klasen et al., "Two distinct regions of the CD28 intracytoplasmic domain are involved in the tyrosine phosphorylation of Vav end GTPase activating protein-associated p62 protein", International Immunology, Jan. 1996, vol. 10, No. 4, pp. 481-489 (9 pages).

Partial Supplementary European Search Report, dated Jun. 8, 2020, for European Application No. 17866638.4.

Razidlo et al., "Supplemental Information: Vav1 as a Central Regulator of Invadopodia Assembly", Current Biology, Jan. 6, 2014, vol. 24, 9 pages.

Razidlo et al., "Vav1 as a Central Regulator of Invadopodia Assembly", Current Biology, Jan. 6, 2014, vol. 24, No. 1, pp. 86-93 (8 pages).

α phospho VAV1

α VAV1

α phospho PLC γ 1

α PLC γ 1

α β actin

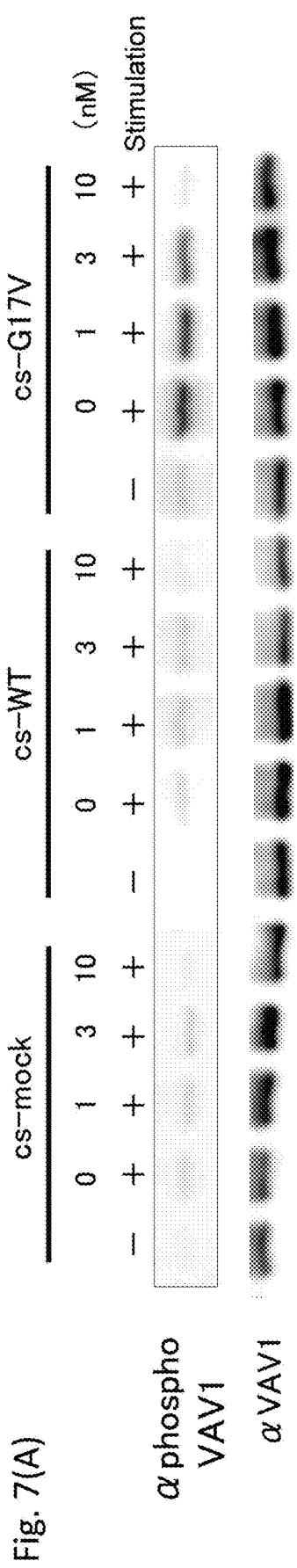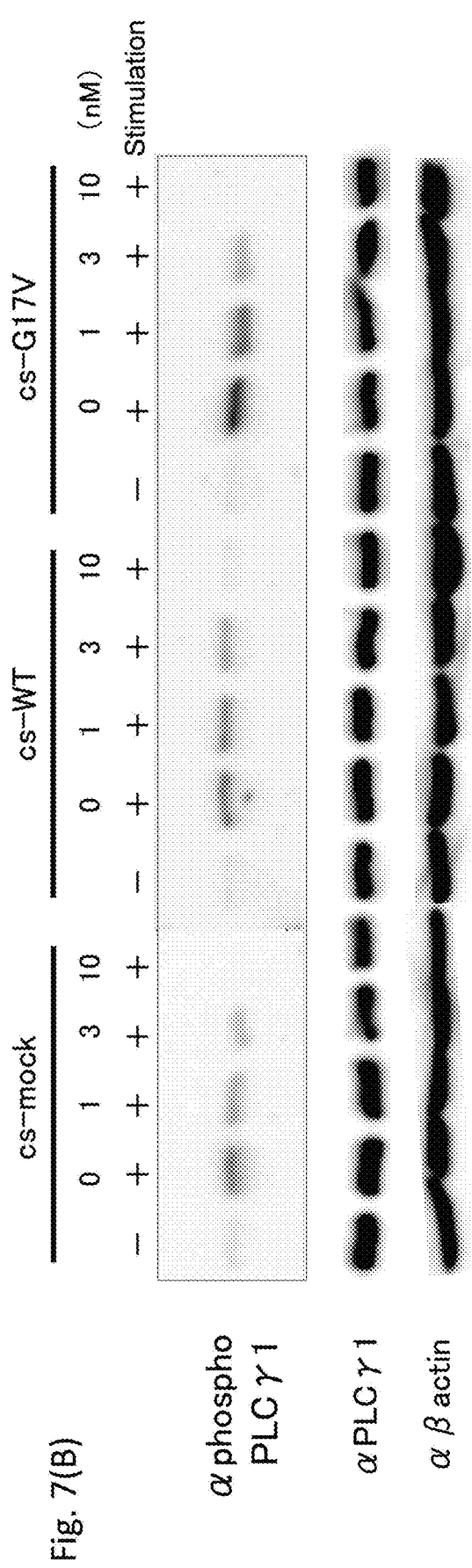
Fig. 7(A)
Fig. 7(B)

* ≦0.05
** ≦0.01
*** ≦0.001

SEQUENCE LISTING

```
<160> NUMBER OF SEQ ID NOS: 8

<210> SEQ ID NO 1
<211> LENGTH: 1943
<212> TYPE: DNA
<213> ORGANISM: Homo sapiens
<220> FEATURE:
<221> NAME/KEY: CDS
<222> LOCATION: (281)..(862)

<400> SEQUENCE: 1
aatagtggat gagctgtgag tgcgcgcgcg tgcgcggggc cgcgacctgt gccggctcga      60
gcccgctggg cactcggagg cgcgcacgtc gttccccgcc ctcccgccgc cgcccgcect     120 cgctctctcg cgctaccctc ccgccgcccg cggtcctccg tcggttctct cgttagtcca     180
cggtctggtc ttcagctacc cgccttcgtc tccgagtttg cgactcgcgg accggcgtcc     240
ccggcgcgaa gaggctggac tcggattcgt tgcctgagca atg gct gcc atc cgg     295
                                              Met Ala Ala Ile Arg
                                              1               5 aag aaa ctg gtg att gtt ggt gat gga gcc tgt gga aag aca tgc ttg     343
Lys Lys Leu Val Ile Val Gly Asp Gly Ala Cys Gly Lys Thr Cys Leu
                10                  15                  20 ctc ata gtc ttc agc aag gac cag ttc cca gag gtg tat gtg ccc aca     391
Leu Ile Val Phe Ser Lys Asp Gln Phe Pro Glu Val Tyr Val Pro Thr
            25                  30                  35 gtg ttt gag aac tat gtg gca gat atc gag gtg gat gga aag cag gta     439
Val Phe Glu Asn Tyr Val Ala Asp Ile Glu Val Asp Gly Lys Gln Val
        40                  45                  50 gag ttg gct ttg tgg gac aca gct ggg cag gaa gat tat gat cgc ctg     487
Glu Leu Ala Leu Trp Asp Thr Ala Gly Gln Glu Asp Tyr Asp Arg Leu
    55                  60                  65
```

```
agg ccc ctc tcc tac cca gat acc gat gtt ata ctg atg tgt ttt tcc      535
Arg Pro Leu Ser Tyr Pro Asp Thr Asp Val Ile Leu Met Cys Phe Ser
 70              75                  80                  85 atc gac agc cct gat agt tta gaa aac atc cca gaa aag tgg acc cca      583
Ile Asp Ser Pro Asp Ser Leu Glu Asn Ile Pro Glu Lys Trp Thr Pro
                 90                  95                 100 gaa gtc aag cat ttc tgt ccc aac gtg ccc atc atc ctg gtt ggg aat      631
Glu Val Lys His Phe Cys Pro Asn Val Pro Ile Ile Leu Val Gly Asn
                    105                 110                 115 aag aag gat ctt cgg aat gat gag cac aca agg cgg gag cta gcc aag      679
Lys Lys Asp Leu Arg Asn Asp Glu His Thr Arg Arg Glu Leu Ala Lys
                120                 125                 130 atg aag cag gag ccg gtg aaa cct gaa gaa ggc aga gat atg gca aac      727
Met Lys Gln Glu Pro Val Lys Pro Glu Glu Gly Arg Asp Met Ala Asn
    135                 140                 145 agg att ggc gct ttt ggg tac atg gag tgt tca gca aag acc aaa gat      775
Arg Ile Gly Ala Phe Gly Tyr Met Glu Cys Ser Ala Lys Thr Lys Asp
150                 155                 160                 165 gga gtg aga gag gtt ttt gaa atg gct acg aga gct gct ctg caa gct      823
Gly Val Arg Glu Val Phe Glu Met Ala Thr Arg Ala Ala Leu Gln Ala
                170                 175                 180 aga cgt ggg aag aaa aaa tct ggg tgc ctt gtc ttg tga aaccttgctg       872
Arg Arg Gly Lys Lys Lys Ser Gly Cys Leu Val Leu
                185                 190 caagcacagc ccttatgcgg ttaattttga agtgctgttt attaatctta gtgtatgatt    932
actggccttt ttcatttatc tataatttac ctaagattac aaatcagaag tcatcttgct   992
accagtattt agaagccaac tatgattatt aacgatgtcc aacccgtctg gcccaccagg   1052
gtccttttga cactgctcta acagccctcc tctgcactcc cacctgacac accaggcgct   1112
aattcaagga atttcttaac ttcttgcttc tttctagaaa gagaaacagt tggtaacttt   1172
tgtgaattag gctgtaacta ctttataact aacatgtcct gcctattatc tgtcagctgc   1232
aaggtactct ggtgagtcac cacttcaggg ctttactccg taacagattt tgttggcata   1292
gctctggggt gggcagtttt ttgaaaatgg gctcaaccag aaaagcccaa gttcatgcag   1352
ctgtggcaga gttacagttc tgtggtttca tgttagttac cttatagtta ctgtgtaatt   1412
agtgccactt aatgtatgtt accaaaaata aatatatcta ccccagacta gatgtagtat   1472
tttttgtata attggatttc ctaatactgt catcctcaaa gaaagtgtat tggttttta    1532 aaaaagaaag tgtatttgga ataaagtca gatggaaaat tcatttttta aattcccgtt    1592
ttgtcacttt ttctgataaa agatggccat attacccctt ttcggcccca tgtatctcag   1652
taccccatgg agctgggcta agtaaatagg aattggtttc acgcctgagg caattagaca   1712
ctttggaaga tggcataacc tgtctcacct ggacttaagc atctggctct aattcacagt   1772
gctcttttct cctcactgta tccaggttcc ctcccagagg agccaccagt tctcatgggt   1832
ggcactcagt ctctcttctc tccagctgac taaactttt ttctgtacca gttaattttt    1892
ccaactacta atagaataaa ggcagttttc taaacttcct gtaaaaaaaa a            1943
```

<210> SEQ ID NO 2
<211> LENGTH: 193
<212> TYPE: PRT
<213> ORGANISM: Homo sapiens -continued

<400> SEQUENCE: 2

```
Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu
```

<210> SEQ ID NO 3
<211> LENGTH: 2944
<212> TYPE: DNA
<213> ORGANISM: Homo sapiens
<220> FEATURE:
<221> NAME/KEY: CDS
<222> LOCATION: (141)..(2678)

<400> SEQUENCE: 3

```
ctctcagggc gacagttaca ggcaaagaag aggaagtggt agcactagct gtcgctccac      60
aggcgagcag ggcaggcgtg cgggcgggtg ggtggtggag gctgcgaggg tgcacggccg     120
gccctgggca ggcggtagcc atg gag ctg tgg cgc caa tgc acc cac tgg ctc    173
                       Met Glu Leu Trp Arg Gln Cys Thr His Trp Leu
                         1               5                   10 atc cag tgc cgg gtg ctg ccg ccc agc cac cgc gtg acc tgg gat ggg       221
Ile Gln Cys Arg Val Leu Pro Pro Ser His Arg Val Thr Trp Asp Gly
            15                  20                  25 gct cag gtg tgt gaa ctg gcc cag gcc ctc cgg gat ggt gtc ctt ctg       269
Ala Gln Val Cys Glu Leu Ala Gln Ala Leu Arg Asp Gly Val Leu Leu
        30                  35                  40 tgt cag ctg ctt aac aac ctg cta ccc cat gcc atc aac ctg cgt gag       317
Cys Gln Leu Leu Asn Asn Leu Leu Pro His Ala Ile Asn Leu Arg Glu
    45                  50                  55 gtc aac ctg cgc ccc cag atg tcc cag ttc ctg tgc ctt aag aac att       365
Val Asn Leu Arg Pro Gln Met Ser Gln Phe Leu Cys Leu Lys Asn Ile
60                  65                  70                  75 aga acc ttc ctg tcc acc tgc tgt gag aag ttc ggc ctc aag cgg agc       413
Arg Thr Phe Leu Ser Thr Cys Cys Glu Lys Phe Gly Leu Lys Arg Ser
                80                  85                  90
```

| | | |
|---|---|---|
| gag ctc ttc gaa gcc ttt gac ctc ttc gat gtg cag gat ttt ggc aag<br>Glu Leu Phe Glu Ala Phe Asp Leu Phe Asp Val Gln Asp Phe Gly Lys<br>95                                     100                            105 | 461 |
| gtc atc tac acc ctg tct gct ctg tcc tgg acc ccg atc gcc cag aac<br>Val Ile Tyr Thr Leu Ser Ala Leu Ser Trp Thr Pro Ile Ala Gln Asn<br>110                       115                     120 | 509 |
| agg ggg atc atg ccc ttc ccc acc gag gag gag agt gta ggt gat gaa<br>Arg Gly Ile Met Pro Phe Pro Thr Glu Glu Glu Ser Val Gly Asp Glu<br>125                    130                     135 | 557 |
| gac atc tac agt ggc ctg tcc gac cag atc gac gac acg gtg gag gag<br>Asp Ile Tyr Ser Gly Leu Ser Asp Gln Ile Asp Asp Thr Val Glu Glu<br>140                    145                    150                    155 | 605 |
| gat gag gac ctg tat gac tgc gtg gag aat gag gag gcg gaa ggc gac<br>Asp Glu Asp Leu Tyr Asp Cys Val Glu Asn Glu Glu Ala Glu Gly Asp<br>                160                    165                    170 | 653 |
| gag atc tat gag gac ctc atg cgc tcg gag ccc gtg tcc atg ccg ccc<br>Glu Ile Tyr Glu Asp Leu Met Arg Ser Glu Pro Val Ser Met Pro Pro<br>175                       180                     185 | 701 |
| aag atg aca gag tat gac aag cgc tgc tgc tgc ctg cgg gag atc cag<br>Lys Met Thr Glu Tyr Asp Lys Arg Cys Cys Cys Leu Arg Glu Ile Gln<br>                190                    195                    200 | 749 |
| cag acg gag gag aag tac act gac acg ctg ggc tcc atc cag cag cat<br>Gln Thr Glu Glu Lys Tyr Thr Asp Thr Leu Gly Ser Ile Gln Gln His<br>205                       210                     215 | 797 |
| ttc ttg aag ccc ctg caa cgg ttc ctg aaa cct caa gac att gag atc<br>Phe Leu Lys Pro Leu Gln Arg Phe Leu Lys Pro Gln Asp Ile Glu Ile<br>220                       225                     230                    235 | 845 |
| atc ttt atc aac att gag gac ctg ctt cgt gtt cat act cac ttc cta<br>Ile Phe Ile Asn Ile Glu Asp Leu Leu Arg Val His Thr His Phe Leu<br>                240                    245                    250 | 893 |
| aag gag atg aag gaa gcc ctg ggc acc cct ggc gca gcc aat ctc tac<br>Lys Glu Met Lys Glu Ala Leu Gly Thr Pro Gly Ala Ala Asn Leu Tyr<br>255                       260                     265 | 941 |
| cag gtc ttc atc aaa tac aag gag agg ttc ctc gtc tat ggc cgc tac<br>Gln Val Phe Ile Lys Tyr Lys Glu Arg Phe Leu Val Tyr Gly Arg Tyr<br>                270                    275                    280 | 989 |
| tgc agc cag gtg gag tca gcc agc aaa cac ctg gac cgt gtg gcc gca<br>Cys Ser Gln Val Glu Ser Ala Ser Lys His Leu Asp Arg Val Ala Ala<br>285                       290                     295 | 1037 |
| gcc cgg gag gac gtg cag atg aag ctg gag gaa tgt tct cag aga gcc<br>Ala Arg Glu Asp Val Gln Met Lys Leu Glu Glu Cys Ser Gln Arg Ala<br>300                       305                     310                    315 | 1085 |
| aac aac ggg agg ttc acc ctg cgg gac ctg ctg atg gtg cct atg cag<br>Asn Asn Gly Arg Phe Thr Leu Arg Asp Leu Leu Met Val Pro Met Gln<br>                320                    325                    330 | 1133 |
| cga gtt ctc aaa tat cac ctc ctt ctc cag gag ctg gtg aaa cac acg<br>Arg Val Leu Lys Tyr His Leu Leu Leu Gln Glu Leu Val Lys His Thr<br>335                       340                     345 | 1181 |
| cag gag gcg atg gag aag gag aac ctg cgg ctg gcc ctg gat gcc atg<br>Gln Glu Ala Met Glu Lys Glu Asn Leu Arg Leu Ala Leu Asp Ala Met<br>                350                    355                    360 | 1229 |
| agg gac ctg gct cag tgc gtg aac gag gtc aag cga gac aac gag aca<br>Arg Asp Leu Ala Gln Cys Val Asn Glu Val Lys Arg Asp Asn Glu Thr<br>365                       370                     375 | 1277 |
| ctg cga cag atc acc aat ttc cag ctg tcc att gag aac ctg gac cag<br>Leu Arg Gln Ile Thr Asn Phe Gln Leu Ser Ile Glu Asn Leu Asp Gln<br>380                       385                     390                    395 | 1325 |
| tct ctg gct cac tat ggc cgg ccc aag atc gac ggg gaa ctc aag atc<br>Ser Leu Ala His Tyr Gly Arg Pro Lys Ile Asp Gly Glu Leu Lys Ile<br>                400                    405                    410 | 1373 |

| | | |
|---|---|---|
| acc tcg gtg gaa cgg cgc tcc aag atg gac agg tat gcc ttc ctg ctc<br>Thr Ser Val Glu Arg Arg Ser Lys Met Asp Arg Tyr Ala Phe Leu Leu<br>415 420 425 | 1421 | |
| gac aaa gct cta ctc atc tgt aag cgc agg gga gac tcc tat gac ctc<br>Asp Lys Ala Leu Leu Ile Cys Lys Arg Arg Gly Asp Ser Tyr Asp Leu<br>430 435 440 | 1469 | |
| aag gac ttt gta aac ctg cac agc ttc cag gtt cgg gat gac tct tca<br>Lys Asp Phe Val Asn Leu His Ser Phe Gln Val Arg Asp Asp Ser Ser<br>445 450 455 | 1517 | |
| gga gac cga gac aac aag aag tgg agc cac atg ttc ctc ctg atc gag<br>Gly Asp Arg Asp Asn Lys Lys Trp Ser His Met Phe Leu Leu Ile Glu<br>460 465 470 475 | 1565 | |
| gac caa ggt gcc cag ggc tat gag ctg ttc ttc aag aca aga gaa ttg<br>Asp Gln Gly Ala Gln Gly Tyr Glu Leu Phe Phe Lys Thr Arg Glu Leu<br>480 485 490 | 1613 | |
| aag aag aag tgg atg gag cag ttt gag atg gcc atc tcc aac atc tat<br>Lys Lys Lys Trp Met Glu Gln Phe Glu Met Ala Ile Ser Asn Ile Tyr<br>495 500 505 | 1661 | |
| ccg gag aat gcc acc gcc aac ggg cat gac ttc cag atg ttc tcc ttt<br>Pro Glu Asn Ala Thr Ala Asn Gly His Asp Phe Gln Met Phe Ser Phe<br>510 515 520 | 1709 | |
| gag gag acc aca tcc tgc aag gcc tgt cag atg ctg ctt aga ggt acc<br>Glu Glu Thr Thr Ser Cys Lys Ala Cys Gln Met Leu Leu Arg Gly Thr<br>525 530 535 | 1757 | |
| ttc tat cag ggc tac cgc tgc cat cgg tgc cgg gca tct gca cac aag<br>Phe Tyr Gln Gly Tyr Arg Cys His Arg Cys Arg Ala Ser Ala His Lys<br>540 545 550 555 | 1805 | |
| gag tgt ctg ggg agg gtc cct cca tgt ggc cga cat ggg caa gat ttc<br>Glu Cys Leu Gly Arg Val Pro Pro Cys Gly Arg His Gly Gln Asp Phe<br>560 565 570 | 1853 | |
| cca gga act atg aag aag gac aaa cta cat cgc agg gct cag gac aaa<br>Pro Gly Thr Met Lys Lys Asp Lys Leu His Arg Arg Ala Gln Asp Lys<br>575 580 585 | 1901 | |
| aag agg aat gag ctg ggt ctg ccc aag atg gag gtg ttt cag gaa tac<br>Lys Arg Asn Glu Leu Gly Leu Pro Lys Met Glu Val Phe Gln Glu Tyr<br>590 595 600 | 1949 | |
| tac ggg ctt cct cca ccc cct gga gcc att gga ccc ttt cta cgg ctc<br>Tyr Gly Leu Pro Pro Pro Pro Gly Ala Ile Gly Pro Phe Leu Arg Leu<br>605 610 615 | 1997 | |
| aac cct gga gac att gtg gag ctc acg aag gct gag gct gaa cag aac<br>Asn Pro Gly Asp Ile Val Glu Leu Thr Lys Ala Glu Ala Glu Gln Asn<br>620 625 630 635 | 2045 | |
| tgg tgg gag ggc aga aat aca tct act aat gaa att ggc tgg ttt cct<br>Trp Trp Glu Gly Arg Asn Thr Ser Thr Asn Glu Ile Gly Trp Phe Pro<br>640 645 650 | 2093 | |
| tgt aac agg gtg aag ccc tat gtc cat ggc cct cct cag gac ctg tct<br>Cys Asn Arg Val Lys Pro Tyr Val His Gly Pro Pro Gln Asp Leu Ser<br>655 660 665 | 2141 | |
| gtt cat ctc tgg tac gca ggc ccc atg gag cgg gca ggg gca gag agc<br>Val His Leu Trp Tyr Ala Gly Pro Met Glu Arg Ala Gly Ala Glu Ser<br>670 675 680 | 2189 | |
| atc ctg gcc aac cgc tcg gac ggg act ttc ttg gtg cgg cag agg gtg<br>Ile Leu Ala Asn Arg Ser Asp Gly Thr Phe Leu Val Arg Gln Arg Val<br>685 690 695 | 2237 | |
| aag gat gca gca gaa ttt gcc atc agc att aaa tat aac gtc gag gtc<br>Lys Asp Ala Ala Glu Phe Ala Ile Ser Ile Lys Tyr Asn Val Glu Val<br>700 705 710 715 | 2285 | |
| aag cac att aaa atc atg aca gca gaa gga ctg tac cgg atc aca gag<br>Lys His Ile Lys Ile Met Thr Ala Glu Gly Leu Tyr Arg Ile Thr Glu<br>720 725 730 | 2333 | |

```
aaa aag gct ttc cgg ggg ctt acg gag ctg gtg gag ttt tac cag cag    2381
Lys Lys Ala Phe Arg Gly Leu Thr Glu Leu Val Glu Phe Tyr Gln Gln
            735                 740                 745 aac tct cta aag gat tgc ttc aag tct ctg gac acc acc ttg cag ttc    2429
Asn Ser Leu Lys Asp Cys Phe Lys Ser Leu Asp Thr Thr Leu Gln Phe
        750                 755                 760 ccc ttc aag gag cct gaa aag aga acc atc agc agg cca gca gtg gga    2477
Pro Phe Lys Glu Pro Glu Lys Arg Thr Ile Ser Arg Pro Ala Val Gly
    765                 770                 775 agc aca aag tat ttt ggc aca gcc aaa gcc cgc tat gac ttc tgc gcc    2525
Ser Thr Lys Tyr Phe Gly Thr Ala Lys Ala Arg Tyr Asp Phe Cys Ala
780                 785                 790                 795 cga gac cga tca gag ctg tcg ctc aag gag ggt gac atc atc aag atc    2573
Arg Asp Arg Ser Glu Leu Ser Leu Lys Glu Gly Asp Ile Ile Lys Ile
                800                 805                 810 ctt aac aag aag gga cag caa ggc tgg tgg cga ggg gag atc tat ggc    2621
Leu Asn Lys Lys Gly Gln Gln Gly Trp Trp Arg Gly Glu Ile Tyr Gly
            815                 820                 825 cgg gtt ggc tgg ttc cct gcc aac tac gtg gag gaa gat tat tct gaa    2669
Arg Val Gly Trp Phe Pro Ala Asn Tyr Val Glu Glu Asp Tyr Ser Glu
        830                 835                 840 tac tgc tga gccctggtgc cttggcagag agacgagaaa ctccaggctc            2718
Tyr Cys
    845 tgagcccggc gtgggcaggc agcggagcca ggggctgtga cagctcccgg cgggtggaga  2778 ctttgggatg gactggagga ggccagcgtc cagctggcgg tgctcccggg atgtgccctg  2838 acatggttaa tttataacac cccgatttcc tcttgggtcc cctcaagcag acggggctca  2898 agggggttac atttaataaa aggatgaaga tggatagaaa aaaaaa                 2944

<210> SEQ ID NO 4
<211> LENGTH: 845
<212> TYPE: PRT
<213> ORGANISM: Homo sapiens

<400> SEQUENCE: 4

Met Glu Leu Trp Arg Gln Cys Thr His Trp Leu Ile Gln Cys Arg Val
1               5                   10                  15

Leu Pro Pro Ser His Arg Val Thr Trp Asp Gly Ala Gln Val Cys Glu
            20                  25                  30

Leu Ala Gln Ala Leu Arg Asp Gly Val Leu Leu Cys Gln Leu Leu Asn
        35                  40                  45

Asn Leu Leu Pro His Ala Ile Asn Leu Arg Glu Val Asn Leu Arg Pro
    50                  55                  60

Gln Met Ser Gln Phe Leu Cys Leu Lys Asn Ile Arg Thr Phe Leu Ser
65                  70                  75                  80

Thr Cys Cys Glu Lys Phe Gly Leu Lys Arg Ser Glu Leu Phe Glu Ala
                85                  90                  95

Phe Asp Leu Phe Asp Val Gln Asp Phe Gly Lys Val Ile Tyr Thr Leu
            100                 105                 110

Ser Ala Leu Ser Trp Thr Pro Ile Ala Gln Asn Arg Gly Ile Met Pro
        115                 120                 125

Phe Pro Thr Glu Glu Glu Ser Val Gly Asp Glu Asp Ile Tyr Ser Gly
    130                 135                 140

Leu Ser Asp Gln Ile Asp Asp Thr Val Glu Glu Asp Glu Asp Leu Tyr
145                 150                 155                 160
```

-continued

```
Asp Cys Val Glu Asn Glu Glu Ala Glu Gly Asp Glu Ile Tyr Glu Asp
            165                 170                 175
Leu Met Arg Ser Glu Pro Val Ser Met Pro Pro Lys Met Thr Glu Tyr
        180                 185                 190
Asp Lys Arg Cys Cys Leu Arg Glu Ile Gln Gln Thr Glu Glu Lys
    195                 200                 205
Tyr Thr Asp Thr Leu Gly Ser Ile Gln Gln His Phe Leu Lys Pro Leu
210                 215                 220
Gln Arg Phe Leu Lys Pro Gln Asp Ile Glu Ile Phe Ile Asn Ile
225                 230                 235                 240
Glu Asp Leu Leu Arg Val His Thr His Phe Leu Lys Glu Met Lys Glu
                245                 250                 255
Ala Leu Gly Thr Pro Gly Ala Ala Asn Leu Tyr Gln Val Phe Ile Lys
            260                 265                 270
Tyr Lys Glu Arg Phe Leu Val Tyr Gly Arg Tyr Cys Ser Gln Val Glu
        275                 280                 285
Ser Ala Ser Lys His Leu Asp Arg Val Ala Ala Arg Glu Asp Val
    290                 295                 300
Gln Met Lys Leu Glu Glu Cys Ser Gln Arg Ala Asn Asn Gly Arg Phe
305                 310                 315                 320
Thr Leu Arg Asp Leu Leu Met Val Pro Met Gln Arg Val Leu Lys Tyr
                325                 330                 335
His Leu Leu Leu Gln Glu Leu Val Lys His Thr Gln Glu Ala Met Glu
            340                 345                 350
Lys Glu Asn Leu Arg Leu Ala Leu Asp Ala Met Arg Asp Leu Ala Gln
        355                 360                 365
Cys Val Asn Glu Val Lys Arg Asp Asn Glu Thr Leu Arg Gln Ile Thr
    370                 375                 380
Asn Phe Gln Leu Ser Ile Glu Asn Leu Asp Gln Ser Leu Ala His Tyr
385                 390                 395                 400
Gly Arg Pro Lys Ile Asp Gly Glu Leu Lys Ile Thr Ser Val Glu Arg
                405                 410                 415
Arg Ser Lys Met Asp Arg Tyr Ala Phe Leu Leu Asp Lys Ala Leu Leu
            420                 425                 430
Ile Cys Lys Arg Arg Gly Asp Ser Tyr Asp Leu Lys Asp Phe Val Asn
        435                 440                 445
Leu His Ser Phe Gln Val Arg Asp Asp Ser Ser Gly Asp Arg Asp Asn
    450                 455                 460
Lys Lys Trp Ser His Met Phe Leu Leu Ile Glu Asp Gln Gly Ala Gln
465                 470                 475                 480
Gly Tyr Glu Leu Phe Phe Lys Thr Arg Glu Leu Lys Lys Lys Trp Met
                485                 490                 495
Glu Gln Phe Glu Met Ala Ile Ser Asn Ile Tyr Pro Glu Asn Ala Thr
            500                 505                 510
Ala Asn Gly His Asp Phe Gln Met Phe Ser Phe Glu Glu Thr Thr Ser
        515                 520                 525
Cys Lys Ala Cys Gln Met Leu Leu Arg Gly Thr Phe Tyr Gln Gly Tyr
    530                 535                 540
Arg Cys His Arg Cys Arg Ala Ser Ala His Lys Glu Cys Leu Gly Arg
545                 550                 555                 560
Val Pro Pro Cys Gly Arg His Gly Gln Asp Phe Pro Gly Thr Met Lys
                565                 570                 575
```

-continued

```
Lys Asp Lys Leu His Arg Arg Ala Gln Asp Lys Lys Arg Asn Glu Leu
            580                 585                 590

Gly Leu Pro Lys Met Glu Val Phe Gln Glu Tyr Tyr Gly Leu Pro Pro
        595                 600                 605

Pro Pro Gly Ala Ile Gly Pro Phe Leu Arg Leu Asn Pro Gly Asp Ile
    610                 615                 620

Val Glu Leu Thr Lys Ala Glu Ala Gln Asn Trp Trp Glu Gly Arg
625                 630                 635                 640

Asn Thr Ser Thr Asn Glu Ile Gly Trp Phe Pro Cys Asn Arg Val Lys
            645                 650                 655

Pro Tyr Val His Gly Pro Pro Gln Asp Leu Ser Val His Leu Trp Tyr
        660                 665                 670

Ala Gly Pro Met Glu Arg Ala Gly Ala Glu Ser Ile Leu Ala Asn Arg
    675                 680                 685

Ser Asp Gly Thr Phe Leu Val Arg Gln Arg Val Lys Asp Ala Ala Glu
    690                 695                 700

Phe Ala Ile Ser Ile Lys Tyr Asn Val Glu Val Lys His Ile Lys Ile
705                 710                 715                 720

Met Thr Ala Glu Gly Leu Tyr Arg Ile Thr Glu Lys Lys Ala Phe Arg
            725                 730                 735

Gly Leu Thr Glu Leu Val Glu Phe Tyr Gln Gln Asn Ser Leu Lys Asp
        740                 745                 750

Cys Phe Lys Ser Leu Asp Thr Thr Leu Gln Phe Pro Phe Lys Glu Pro
    755                 760                 765

Glu Lys Arg Thr Ile Ser Arg Pro Ala Val Gly Ser Thr Lys Tyr Phe
    770                 775                 780

Gly Thr Ala Lys Ala Arg Tyr Asp Phe Cys Ala Arg Asp Arg Ser Glu
785                 790                 795                 800

Leu Ser Leu Lys Glu Gly Asp Ile Ile Lys Ile Leu Asn Lys Lys Gly
            805                 810                 815

Gln Gln Gly Trp Trp Arg Gly Glu Ile Tyr Gly Arg Val Gly Trp Phe
        820                 825                 830

Pro Ala Asn Tyr Val Glu Glu Asp Tyr Ser Glu Tyr Cys
    835                 840                 845

<210> SEQ ID NO 5
<211> LENGTH: 4865
<212> TYPE: DNA
<213> ORGANISM: Homo sapiens
<220> FEATURE:
<221> NAME/KEY: CDS
<222> LOCATION: (47)..(2683)

<400> SEQUENCE: 5
actttggctc gagcactgcc ctgagccggt cgggcccgcg ggcgcc atg gag cag        55
                                                Met Glu Gln
                                                1 tgg cgg cag tgc ggc cgc tgg ctc atc gat tgc aag gtc ctg ccg ccc      103
Trp Arg Gln Cys Gly Arg Trp Leu Ile Asp Cys Lys Val Leu Pro Pro
    5                  10                  15 aac cac cgg gtg gtg tgg ccc tcg gcc gtg gtc ttc gac ctg gcg cag      151
Asn His Arg Val Val Trp Pro Ser Ala Val Val Phe Asp Leu Ala Gln
20                  25                  30                  35 gcg ctg cgc gac ggg gtc ctt ctg tgc cag ctg ctg cac aac ctc tcc      199
Ala Leu Arg Asp Gly Val Leu Leu Cys Gln Leu Leu His Asn Leu Ser
                40                  45                  50
```

```
ccc ggc tcc atc gac ctc aag gac atc aac ttc cgg ccg cag atg tcc      247
Pro Gly Ser Ile Asp Leu Lys Asp Ile Asn Phe Arg Pro Gln Met Ser
            55                  60                  65 cag ttt ctg tgt ttg aag aac ata cgc acc ttc ctg aaa gtc tgc cac      295
Gln Phe Leu Cys Leu Lys Asn Ile Arg Thr Phe Leu Lys Val Cys His
        70                  75                  80 gat aaa ttt gga tta agg aac agc gag ctg ttt gac ccc ttt gac ctc      343
Asp Lys Phe Gly Leu Arg Asn Ser Glu Leu Phe Asp Pro Phe Asp Leu
85                  90                  95 ttc gat gtg cga gac ttt gga aag gtc atc tcc gcg gtg tcg agg ctc      391
Phe Asp Val Arg Asp Phe Gly Lys Val Ile Ser Ala Val Ser Arg Leu
100                 105                 110                 115 tcc ctg cac agc atc gcg cag aac aaa ggg atc agg cct ttt ccc tca      439
Ser Leu His Ser Ile Ala Gln Asn Lys Gly Ile Arg Pro Phe Pro Ser
            120                 125                 130 gag gag acc aca gag aat gac gat gac gtc tac cgc agc ctg gag gag      487
Glu Glu Thr Thr Glu Asn Asp Asp Asp Val Tyr Arg Ser Leu Glu Glu
        135                 140                 145 ctg gcc gac gag cat gac ctg ggg gag gac atc tac gac tgc gtc ccg      535
Leu Ala Asp Glu His Asp Leu Gly Glu Asp Ile Tyr Asp Cys Val Pro
                150                 155                 160 tgt gag gat gga ggg gac gac atc tac gag gac atc atc aag gtg gag      583
Cys Glu Asp Gly Gly Asp Asp Ile Tyr Glu Asp Ile Ile Lys Val Glu
165                 170                 175 gtg cag cag ccc atg att aga tac atg cag aaa atg ggc atg act gaa      631
Val Gln Gln Pro Met Ile Arg Tyr Met Gln Lys Met Gly Met Thr Glu
180                 185                 190                 195 gat gac aag agg aac tgc tgc ctg ctg gag atc cag gag acc gag gcc      679
Asp Asp Lys Arg Asn Cys Cys Leu Leu Glu Ile Gln Glu Thr Glu Ala
            200                 205                 210 aag tac tac cgc acc ctg gag gac att gag aag aac tac atg agc ccc      727
Lys Tyr Tyr Arg Thr Leu Glu Asp Ile Glu Lys Asn Tyr Met Ser Pro
        215                 220                 225 ctg cgg ctg gtg ctg agc ccg gcg gac atg gca gct gtc ttc att aac      775
Leu Arg Leu Val Leu Ser Pro Ala Asp Met Ala Ala Val Phe Ile Asn
                230                 235                 240 ctg gag gac ctg atc aag gtg cat cac agc ttc ctg agg gcc atc gac      823
Leu Glu Asp Leu Ile Lys Val His His Ser Phe Leu Arg Ala Ile Asp
245                 250                 255 gtg tcc gtg atg gtg ggg ggc agc acg ctg gcc aag gtc ttc ctc gat      871
Val Ser Val Met Val Gly Gly Ser Thr Leu Ala Lys Val Phe Leu Asp
260                 265                 270                 275 ttc aag gaa agg ctt ctg atc tac ggg gag tac tgc agc cac atg gag      919
Phe Lys Glu Arg Leu Leu Ile Tyr Gly Glu Tyr Cys Ser His Met Glu
            280                 285                 290 cac gcc cag aac aca ctg aac cag ctc ctg gcc agc cgg gag gac ttc      967
His Ala Gln Asn Thr Leu Asn Gln Leu Leu Ala Ser Arg Glu Asp Phe
        295                 300                 305 agg cag aaa gtc gag gag tgc aca ctg aag gtc cag gat gga aaa ttt     1015
Arg Gln Lys Val Glu Glu Cys Thr Leu Lys Val Gln Asp Gly Lys Phe
                310                 315                 320 aag ctg caa gac ctg ctg gtg gtc ccc atg cag agg gtg ctc aaa tac     1063
Lys Leu Gln Asp Leu Leu Val Val Pro Met Gln Arg Val Leu Lys Tyr
325                 330                 335 cac ctg ctc ttg aag gag ctt ctg agc cat tct gcg gaa cgg cct gag     1111
His Leu Leu Leu Lys Glu Leu Leu Ser His Ser Ala Glu Arg Pro Glu
340                 345                 350                 355 agg cag cag ctc aaa gaa gca ctg gaa gcc atg cag gac ttg gcg atg     1159
Arg Gln Gln Leu Lys Glu Ala Leu Glu Ala Met Gln Asp Leu Ala Met
            360                 365                 370
```

-continued

| | |
|---|---|
| tac atc aat gaa gtt aaa cgg gac aag gag acc ttg agg aaa atc agc<br>Tyr Ile Asn Glu Val Lys Arg Asp Lys Glu Thr Leu Arg Lys Ile Ser<br>375 380 385 | 1207 |
| gaa ttt cag agt tct ata gaa aat ttg caa gtg aaa ctg gag gaa ttt<br>Glu Phe Gln Ser Ser Ile Glu Asn Leu Gln Val Lys Leu Glu Glu Phe<br>390 395 400 | 1255 |
| gga aga cca aag att gac ggg gaa ctg aaa gtc cgg tcc ata gtc aac<br>Gly Arg Pro Lys Ile Asp Gly Glu Leu Lys Val Arg Ser Ile Val Asn<br>405 410 415 | 1303 |
| cac acc aag cag gac agg tac ttg ttc ctg ttt gac aag gtg gtc atc<br>His Thr Lys Gln Asp Arg Tyr Leu Phe Leu Phe Asp Lys Val Val Ile<br>420 425 430 435 | 1351 |
| gtc tgc aag cgg aag ggc tac agc tac gag ctc aag gag atc atc gag<br>Val Cys Lys Arg Lys Gly Tyr Ser Tyr Glu Leu Lys Glu Ile Ile Glu<br>440 445 450 | 1399 |
| ctg ctg ttc cac aag atg acc gac gac ccc atg aac aac aag gac gtc<br>Leu Leu Phe His Lys Met Thr Asp Asp Pro Met Asn Asn Lys Asp Val<br>455 460 465 | 1447 |
| aag aag tct cac ggg aaa atg tgg tcc tac ggc ttc tac cta att cac<br>Lys Lys Ser His Gly Lys Met Trp Ser Tyr Gly Phe Tyr Leu Ile His<br>470 475 480 | 1495 |
| ctt caa gga aag cag ggc ttc cag ttt ttc tgc aaa aca gaa gat atg<br>Leu Gln Gly Lys Gln Gly Phe Gln Phe Phe Cys Lys Thr Glu Asp Met<br>485 490 495 | 1543 |
| aag agg aag tgg atg gag cag ttt gag atg gcc atg tca aac atc aag<br>Lys Arg Lys Trp Met Glu Gln Phe Glu Met Ala Met Ser Asn Ile Lys<br>500 505 510 515 | 1591 |
| cca gac aaa gcc aat gcc aac cac cac agt ttc cag atg tac acg ttt<br>Pro Asp Lys Ala Asn Ala Asn His His Ser Phe Gln Met Tyr Thr Phe<br>520 525 530 | 1639 |
| gac aag acc acc aac tgc aaa gcc tgc aaa atg ttc ctc agg ggc acc<br>Asp Lys Thr Thr Asn Cys Lys Ala Cys Lys Met Phe Leu Arg Gly Thr<br>535 540 545 | 1687 |
| ttc tac cag gga tac atg tgt acc aag tgt ggc gtc ggg gca cac aag<br>Phe Tyr Gln Gly Tyr Met Cys Thr Lys Cys Gly Val Gly Ala His Lys<br>550 555 560 | 1735 |
| gag tgc ctg gaa gtg ata cct ccc tgc aag ttc act tct cct gca gat<br>Glu Cys Leu Glu Val Ile Pro Pro Cys Lys Phe Thr Ser Pro Ala Asp<br>565 570 575 | 1783 |
| ctg gac gcc tcc gga gcg gga cca ggt ccc aag atg gtg gcc atg cag<br>Leu Asp Ala Ser Gly Ala Gly Pro Gly Pro Lys Met Val Ala Met Gln<br>580 585 590 595 | 1831 |
| aat tac cat ggc aac cca gcc cct ccc ggg aag cct gtg ctg acc ttc<br>Asn Tyr His Gly Asn Pro Ala Pro Pro Gly Lys Pro Val Leu Thr Phe<br>600 605 610 | 1879 |
| cag acg ggc gac gtg ctt gag ctg ctg agg ggc gac cct gag tct ccg<br>Gln Thr Gly Asp Val Leu Glu Leu Leu Arg Gly Asp Pro Glu Ser Pro<br>615 620 625 | 1927 |
| tgg tgg gag ggt cgt ctg gta caa acc agg aag tca ggg tat ttc ccc<br>Trp Trp Glu Gly Arg Leu Val Gln Thr Arg Lys Ser Gly Tyr Phe Pro<br>630 635 640 | 1975 |
| agc tca tct gtg aag ccc tgc cct gtg gat gga agg ccg ccc atc agc<br>Ser Ser Ser Val Lys Pro Cys Pro Val Asp Gly Arg Pro Pro Ile Ser<br>645 650 655 | 2023 |
| cgg ccg cca tcc cgg gag atc gac tac act gca tac ccc tgg ttt gca<br>Arg Pro Pro Ser Arg Glu Ile Asp Tyr Thr Ala Tyr Pro Trp Phe Ala<br>660 665 670 675 | 2071 |
| ggt aac atg gag agg cag cag acg gac aac ctg ctc aag tcc cac gcc<br>Gly Asn Met Glu Arg Gln Gln Thr Asp Asn Leu Leu Lys Ser His Ala<br>680 685 690 | 2119 |

```
agc ggg acc tac ctg atc agg gag cgg cct gcc gag gct gag cgc ttt    2167
Ser Gly Thr Tyr Leu Ile Arg Glu Arg Pro Ala Glu Ala Glu Arg Phe
            695                 700                 705 gca ata agc atc aag ttc aat gat gag gtg aag cac atc aag gtg gtg    2215
Ala Ile Ser Ile Lys Phe Asn Asp Glu Val Lys His Ile Lys Val Val
            710                 715                 720 gag aag gac aac tgg atc cac atc aca gag gcc aag aaa ttc gac agc    2263
Glu Lys Asp Asn Trp Ile His Ile Thr Glu Ala Lys Lys Phe Asp Ser
        725                 730                 735 ctc ctg gag ttg gtg gag tac tac cag tgc cac tca ctg aag gag agc    2311
Leu Leu Glu Leu Val Glu Tyr Tyr Gln Cys His Ser Leu Lys Glu Ser
740                 745                 750                 755 ttc aag cag ctg gac acc aca ctc aag tac ccc tac aag tcc cgg gaa    2359
Phe Lys Gln Leu Asp Thr Thr Leu Lys Tyr Pro Tyr Lys Ser Arg Glu
                760                 765                 770 cgt tcg gcc tcc agg gcc tcc agc cgg tcc cca gct tcc tgt gct tcc    2407
Arg Ser Ala Ser Arg Ala Ser Ser Arg Ser Pro Ala Ser Cys Ala Ser
            775                 780                 785 tac aac ttt tct ttt ctc agt cct cag ggc ctc agc ttt gct tct cag    2455
Tyr Asn Phe Ser Phe Leu Ser Pro Gln Gly Leu Ser Phe Ala Ser Gln
            790                 795                 800 ggc ccc tcc gct ccc ttc tgg tca gtg ttc acg ccc cgc gtc atc ggc    2503
Gly Pro Ser Ala Pro Phe Trp Ser Val Phe Thr Pro Arg Val Ile Gly
805                 810                 815 aca gct gtg gcc agg tat aac ttt gcc gcc cga gat atg agg gag ctt    2551
Thr Ala Val Ala Arg Tyr Asn Phe Ala Ala Arg Asp Met Arg Glu Leu
820                 825                 830                 835 tcg ctg cgg gag ggt gac gtg gtg agg atc tac agc cgc atc ggc gga    2599
Ser Leu Arg Glu Gly Asp Val Val Arg Ile Tyr Ser Arg Ile Gly Gly
                840                 845                 850 gac cag ggc tgg tgg aag ggc gag acc aac gga cgg att ggc tgg ttt    2647
Asp Gln Gly Trp Trp Lys Gly Glu Thr Asn Gly Arg Ile Gly Trp Phe
            855                 860                 865 cct tca acg tac gta gaa gag gag ggc atc cag tga cggcaggaac         2693
Pro Ser Thr Tyr Val Glu Glu Glu Gly Ile Gln
            870                 875 gtggacaaga ctcgcagatt ttcttgggag agtcactcca gccctgaagt ctgtctctag  2753
ctcctctgtg actcagaggg gaaataccaa cctcccagtc ttccactgcc cacagggata  2813
gggagggtgt tgagaatcct aaactcgaac cgtttcactg tcagcctgcc ctcggcgacc  2873
catcactggg tatgctattg tacatagagg aaacctgggc tagccccacc cagagcgcag  2933
aggagggggc accgacagcg ctgcgagcca ggctctgggt agtggctgag gccagaggcc  2993
catcgcctgc ccctgtccaa ctgagatggc cttcaggagc ctaggtttga acagcagatg  3053
ctgtcccagg aagggctagg gacatcggag gggacctgcc cccacaccct ctgctcagcc  3113
cctggactca gccttgcctg tcttttcctg ctgctcccag ggggaggtgt cagacctcgg  3173
gaggcagacg ggaccagagc caggctgttc actgtgggcc cacttgcccc actgtgctag  3233
ggcgcgggag gagagagcac tgtggtcgcc ctctgcagcc actctggctc caagacttc   3293
cctgactccc ccactcccct ccttgccagg ggcacacccg accccacac ggcaggcccc   3353
tctcttggga ggggcctttg gaatgatgaa attccaaccc tgctgcccgg tcagcggtac  3413
cgtttcctgc cctctctctg agaggccctt tctggagtcc tgggaaggtg tctgcctggc  3473
cgcgctgcca gatcagtaca tcttttgtaa aaaccctgaa atgggcaggg aagaaaacag  3533
ggatttcccc tctctagatc cctgccaggt ccctctccag gaggccctc tgctctcctg   3593
aagggtggtc cctgagggtc tgcccagcct tggcacgaga ggttggttcc agcccctggc  3653
```

-continued

```
aggggcttcct tccaagggcc cctgcagcct acaaactggg cctcgggcga ctcaaaataa    3713
gtgctcttgg gggtggctct acccccattac ctcccccagc cacaactcct ggccttcgac    3773
ttctggctgg gttagccaga ccctggtttc tctaccctga tgttgcatga gacctggtaa    3833
cagtgtctcc ctcccagctc cttgccaaag cctctgttga gacctgggct tcttgtagcc    3893
ccttctccct ctggccagct gcacagcctg tgggaggtgc ccggcccagg ctgggtgtgg    3953
gggaagctgg tccctgctgt gggtggcgct ggggacctag gggctccttc tgaggttggc    4013
cttgtggcct ctgggctgta tgcctctggg gtgtagggaa gaggcgggag gagtcatggg    4073
gatggggagc ggcaggggga gagggggcc ctcgacaaag cttgggaaa tgaggggagg    4133 tggaggcagg gcagggaag cgaagagtca gccttggaga gagcaccctg gggcctccgt    4193
gtcggggtac acccagcact ttgcgacctg cggcccagca ggcgcggagg atggcgggga    4253
ggaagccagc agcccctgtg tttactgtcg tcagaaaggt cttgtgtttt ggttttgggg    4313 ttttttgtttt gtttgtgttt tgtttggctt gtttgttttt taaggggaaa aaagtttgta    4373
attatttcat ccaaatctcc cgttatatat ctgtgaataa taagagattt tataatagca    4433
agaaaatgat gtatatttta gtttgttgac aaataagtca tcatgatcac gaaggacact    4493
gagaaaaaat aatttagaac cctggttttt gtgaattttt ttgttttgtg tttctttgtt    4553
ttgagatttg tgtttggttt ggttttttgca ctgcactaag gcaggagggt tggagggctg    4613
ggtgcagcct gggagtccga tggttttcag caggagacgg ggtgtcccct gcaggggct    4673 aaactgcagg ggcctgagat tagctgtgaa catgtgggag cccgatgcat gtgggtcagg    4733
gatctggggg cccccccagc tggcgggaac cccaaatgga cacaaactgt acatttgcca    4793
atgggttttt ttcagaccat ggttttact tgcaaataaa cctgagttct tttctgcaaa    4853
aaaaaaaaaa aa                                                        4865
```

<210> SEQ ID NO 6
<211> LENGTH: 878
<212> TYPE: PRT
<213> ORGANISM: Homo sapiens

<400> SEQUENCE: 6

Met Glu Gln Trp Arg Gln Cys Gly Arg Trp Leu Ile Asp Cys Lys Val
1               5                   10                  15

Leu Pro Pro Asn His Arg Val Val Trp Pro Ser Ala Val Val Phe Asp
            20                  25                  30

Leu Ala Gln Ala Leu Arg Asp Gly Val Leu Leu Cys Gln Leu Leu His
        35                  40                  45

Asn Leu Ser Pro Gly Ser Ile Asp Leu Lys Asp Ile Asn Phe Arg Pro
    50                  55                  60

Gln Met Ser Gln Phe Leu Cys Leu Lys Asn Ile Arg Thr Phe Leu Lys
65                  70                  75                  80

Val Cys His Asp Lys Phe Gly Leu Arg Asn Ser Glu Leu Phe Asp Pro
                85                  90                  95

Phe Asp Leu Phe Asp Val Arg Asp Phe Gly Lys Val Ile Ser Ala Val
            100                 105                 110

Ser Arg Leu Ser Leu His Ser Ile Ala Gln Asn Lys Gly Ile Arg Pro
        115                 120                 125

Phe Pro Ser Glu Glu Thr Thr Glu Asn Asp Asp Asp Val Tyr Arg Ser
    130                 135                 140

Leu Glu Glu Leu Ala Asp Glu His Asp Leu Gly Glu Asp Ile Tyr Asp
145                 150                 155                 160

```
Cys Val Pro Cys Glu Asp Gly Gly Asp Asp Ile Tyr Glu Asp Ile Ile
            165                 170                 175

Lys Val Glu Val Gln Gln Pro Met Ile Arg Tyr Met Gln Lys Met Gly
        180                 185                 190

Met Thr Glu Asp Asp Lys Arg Asn Cys Cys Leu Leu Glu Ile Gln Glu
        195                 200                 205

Thr Glu Ala Lys Tyr Tyr Arg Thr Leu Glu Asp Ile Glu Lys Asn Tyr
        210                 215                 220

Met Ser Pro Leu Arg Leu Val Leu Ser Pro Ala Asp Met Ala Ala Val
225                 230                 235                 240

Phe Ile Asn Leu Glu Asp Leu Ile Lys Val His His Ser Phe Leu Arg
            245                 250                 255

Ala Ile Asp Val Ser Val Met Val Gly Gly Ser Thr Leu Ala Lys Val
            260                 265                 270

Phe Leu Asp Phe Lys Glu Arg Leu Leu Ile Tyr Gly Glu Tyr Cys Ser
            275                 280                 285

His Met Glu His Ala Gln Asn Thr Leu Asn Gln Leu Leu Ala Ser Arg
        290                 295                 300

Glu Asp Phe Arg Gln Lys Val Glu Glu Cys Thr Leu Lys Val Gln Asp
305                 310                 315                 320

Gly Lys Phe Lys Leu Gln Asp Leu Leu Val Val Pro Met Gln Arg Val
            325                 330                 335

Leu Lys Tyr His Leu Leu Leu Lys Glu Leu Leu Ser His Ser Ala Glu
            340                 345                 350

Arg Pro Glu Arg Gln Gln Leu Lys Glu Ala Leu Glu Ala Met Gln Asp
        355                 360                 365

Leu Ala Met Tyr Ile Asn Glu Val Lys Arg Asp Lys Glu Thr Leu Arg
        370                 375                 380

Lys Ile Ser Glu Phe Gln Ser Ser Ile Glu Asn Leu Gln Val Lys Leu
385                 390                 395                 400

Glu Glu Phe Gly Arg Pro Lys Ile Asp Gly Glu Leu Lys Val Arg Ser
            405                 410                 415

Ile Val Asn His Thr Lys Gln Asp Arg Tyr Leu Phe Leu Phe Asp Lys
            420                 425                 430

Val Val Ile Val Cys Lys Arg Lys Gly Tyr Ser Tyr Glu Leu Lys Glu
            435                 440                 445

Ile Ile Glu Leu Leu Phe His Lys Met Thr Asp Asp Pro Met Asn Asn
        450                 455                 460

Lys Asp Val Lys Lys Ser His Gly Lys Met Trp Ser Tyr Gly Phe Tyr
465                 470                 475                 480

Leu Ile His Leu Gln Gly Lys Gln Gly Phe Gln Phe Cys Lys Thr
            485                 490                 495

Glu Asp Met Lys Arg Lys Trp Met Glu Gln Phe Glu Met Ala Met Ser
                500                 505                 510

Asn Ile Lys Pro Asp Lys Ala Asn Ala Asn His His Ser Phe Gln Met
        515                 520                 525

Tyr Thr Phe Asp Lys Thr Thr Asn Cys Lys Ala Cys Lys Met Phe Leu
        530                 535                 540

Arg Gly Thr Phe Tyr Gln Gly Tyr Met Cys Thr Lys Cys Gly Val Gly
545                 550                 555                 560

Ala His Lys Glu Cys Leu Glu Val Ile Pro Pro Cys Lys Phe Thr Ser
            565                 570                 575
```

-continued

```
Pro Ala Asp Leu Asp Ala Ser Gly Ala Gly Pro Gly Pro Lys Met Val
            580                 585                 590
Ala Met Gln Asn Tyr His Gly Asn Pro Ala Pro Gly Lys Pro Val
        595                 600                 605
Leu Thr Phe Gln Thr Gly Asp Val Leu Glu Leu Leu Arg Gly Asp Pro
            610                 615                 620
Glu Ser Pro Trp Trp Glu Gly Arg Leu Val Gln Thr Arg Lys Ser Gly
625                 630                 635                 640
Tyr Phe Pro Ser Ser Ser Val Lys Pro Cys Pro Val Asp Gly Arg Pro
                645                 650                 655
Pro Ile Ser Arg Pro Pro Ser Arg Glu Ile Asp Tyr Thr Ala Tyr Pro
            660                 665                 670
Trp Phe Ala Gly Asn Met Glu Arg Gln Gln Thr Asp Asn Leu Leu Lys
        675                 680                 685
Ser His Ala Ser Gly Thr Tyr Leu Ile Arg Glu Arg Pro Ala Glu Ala
    690                 695                 700
Glu Arg Phe Ala Ile Ser Ile Lys Phe Asn Asp Glu Val Lys His Ile
705                 710                 715                 720
Lys Val Val Glu Lys Asp Asn Trp Ile His Ile Thr Glu Ala Lys Lys
                725                 730                 735
Phe Asp Ser Leu Leu Glu Leu Val Glu Tyr Tyr Gln Cys His Ser Leu
            740                 745                 750
Lys Glu Ser Phe Lys Gln Leu Asp Thr Thr Leu Lys Tyr Pro Tyr Lys
        755                 760                 765
Ser Arg Glu Arg Ser Ala Ser Arg Ala Ser Ser Arg Ser Pro Ala Ser
    770                 775                 780
Cys Ala Ser Tyr Asn Phe Ser Phe Leu Ser Pro Gln Gly Leu Ser Phe
785                 790                 795                 800
Ala Ser Gln Gly Pro Ser Ala Pro Phe Trp Ser Val Phe Thr Pro Arg
                805                 810                 815
Val Ile Gly Thr Ala Val Ala Arg Tyr Asn Phe Ala Ala Arg Asp Met
            820                 825                 830
Arg Glu Leu Ser Leu Arg Glu Gly Asp Val Val Arg Ile Tyr Ser Arg
        835                 840                 845
Ile Gly Gly Asp Gln Gly Trp Trp Lys Gly Glu Thr Asn Gly Arg Ile
    850                 855                 860
Gly Trp Phe Pro Ser Thr Tyr Val Glu Glu Glu Gly Ile Gln
865                 870                 875

<210> SEQ ID NO 7
<211> LENGTH: 4776
<212> TYPE: DNA
<213> ORGANISM: Homo sapiens
<220> FEATURE:
<221> NAME/KEY: CDS
<222> LOCATION: (55)..(2598)

<400> SEQUENCE: 7
cggccgcatc cttgccgccc gccccggccc agccgcgtcc cggagccgtc gggc atg        57
                                                            Met
                                                            1 gag ccg tgg aag cag tgc gcg cag tgg ctc atc cat tgc aag gtg ctg       105
Glu Pro Trp Lys Gln Cys Ala Gln Trp Leu Ile His Cys Lys Val Leu
        5                   10                  15 ccc acc aac cac cgg gtg acc tgg gac tcg gct cag gtg ttc gac ctt       153
Pro Thr Asn His Arg Val Thr Trp Asp Ser Ala Gln Val Phe Asp Leu
    20                  25                  30
```

-continued

| | |
|---|---|
| gcg cag acc ctc cgc gat gga gtc ctg ctc tgc cag ctg ctt aac aac<br>Ala Gln Thr Leu Arg Asp Gly Val Leu Leu Cys Gln Leu Leu Asn Asn<br>35                    40                      45 | 201 |
| ctc cgg gcg cac tcc atc aac ctg aag gag atc aac ctg agg ccg cag<br>Leu Arg Ala His Ser Ile Asn Leu Lys Glu Ile Asn Leu Arg Pro Gln<br>50                    55                    60                    65 | 249 |
| atg tcc cag ttt ctc tgt ttg aag aac ata agg aca ttt ctc acg gcc<br>Met Ser Gln Phe Leu Cys Leu Lys Asn Ile Arg Thr Phe Leu Thr Ala<br>                    70                    75                    80 | 297 |
| tgt tgt gag acg ttt gga atg agg aaa agt gaa ctt ttc gag gca ttt<br>Cys Cys Glu Thr Phe Gly Met Arg Lys Ser Glu Leu Phe Glu Ala Phe<br>                  85                    90                    95 | 345 |
| gac ttg ttt gat gtt cgt gac ttt gga aag gtt ata gaa aca tta tca<br>Asp Leu Phe Asp Val Arg Asp Phe Gly Lys Val Ile Glu Thr Leu Ser<br>              100                    105                    110 | 393 |
| cga ctt tct cga aca cct ata gca ttg gcc aca gga atc agg ccc ttc<br>Arg Leu Ser Arg Thr Pro Ile Ala Leu Ala Thr Gly Ile Arg Pro Phe<br>115                    120                    125 | 441 |
| cca aca gaa gaa agc att aat gat gaa gac atc tac aaa ggc ctt cct<br>Pro Thr Glu Glu Ser Ile Asn Asp Glu Asp Ile Tyr Lys Gly Leu Pro<br>130                    135                    140                    145 | 489 |
| gat tta ata gat gaa acc ctt gtg gaa gat gaa gaa gat ctc tat gac<br>Asp Leu Ile Asp Glu Thr Leu Val Glu Asp Glu Glu Asp Leu Tyr Asp<br>              150                    155                    160 | 537 |
| tgt gtt tat ggg gaa gat gaa ggt gga gaa gtc tat gag gac tta atg<br>Cys Val Tyr Gly Glu Asp Glu Gly Gly Glu Val Tyr Glu Asp Leu Met<br>                  165                    170                    175 | 585 |
| aag gca gag gaa gca cat cag ccc aaa tgt cca gaa aat gat ata cga<br>Lys Ala Glu Glu Ala His Gln Pro Lys Cys Pro Glu Asn Asp Ile Arg<br>180                    185                    190 | 633 |
| agt tgt tgt cta gca gaa att aag cag aca gaa gaa aaa tat aca gaa<br>Ser Cys Cys Leu Ala Glu Ile Lys Gln Thr Glu Glu Lys Tyr Thr Glu<br>195                    200                    205 | 681 |
| act ttg gag tca ata gaa aag tat ttc atg gca cca cta aaa aga ttt<br>Thr Leu Glu Ser Ile Glu Lys Tyr Phe Met Ala Pro Leu Lys Arg Phe<br>210                    215                    220                    225 | 729 |
| ctg aca gca gca gaa ttt gat tca gta ttc atc aac att cct gaa ctt<br>Leu Thr Ala Ala Glu Phe Asp Ser Val Phe Ile Asn Ile Pro Glu Leu<br>              230                    235                    240 | 777 |
| gta aaa ctt cat cgg aac cta atg caa gag att cat gat tcc att gta<br>Val Lys Leu His Arg Asn Leu Met Gln Glu Ile His Asp Ser Ile Val<br>                  245                    250                    255 | 825 |
| aat aaa aat gac cag aac ttg tac caa gtt ttt att aac tac aag gaa<br>Asn Lys Asn Asp Gln Asn Leu Tyr Gln Val Phe Ile Asn Tyr Lys Glu<br>260                    265                    270 | 873 |
| aga ttg gtt att tac ggg cag tac tgc agt gga gtg gag tca gcc atc<br>Arg Leu Val Ile Tyr Gly Gln Tyr Cys Ser Gly Val Glu Ser Ala Ile<br>275                    280                    285 | 921 |
| tct agt tta gac tac att tct aag aca aaa gaa gat gtc aaa ctg aaa<br>Ser Ser Leu Asp Tyr Ile Ser Lys Thr Lys Glu Asp Val Lys Leu Lys<br>290                    295                    300                    305 | 969 |
| tta gag gaa tgt tcc aaa aga gca aat aat ggg aaa ttt act ctt cga<br>Leu Glu Glu Cys Ser Lys Arg Ala Asn Asn Gly Lys Phe Thr Leu Arg<br>              310                    315                    320 | 1017 |
| gac ttg ctt gtg gtt cct atg caa cgt gtt tta aag tac cac ctt ctc<br>Asp Leu Leu Val Val Pro Met Gln Arg Val Leu Lys Tyr His Leu Leu<br>                  325                    330                    335 | 1065 |
| ctc cag gaa ctg gtc aaa cat acc act gat ccg act gag aag gca aat<br>Leu Gln Glu Leu Val Lys His Thr Thr Asp Pro Thr Glu Lys Ala Asn<br>340                    345                    350 | 1113 |

```
ctg aaa ctg gct ctt gat gcc atg aag gac ttg gca caa tat gtg aat    1161
Leu Lys Leu Ala Leu Asp Ala Met Lys Asp Leu Ala Gln Tyr Val Asn
355             360                 365 gaa gtg aaa aga gat aat gag acc ctt cgt gaa att aaa cag ttt cag    1209
Glu Val Lys Arg Asp Asn Glu Thr Leu Arg Glu Ile Lys Gln Phe Gln
370                 375                 380             385 cta tct ata gag aat ttg aac caa cca gtt ttg ctt ttt gga cga cct    1257
Leu Ser Ile Glu Asn Leu Asn Gln Pro Val Leu Leu Phe Gly Arg Pro
                390                 395                 400 cag gga gat ggt gaa att cga ata acc act cta gac aag cat acc aaa    1305
Gln Gly Asp Gly Glu Ile Arg Ile Thr Thr Leu Asp Lys His Thr Lys
            405                 410                 415 caa gaa agg cat atc ttc tta ttt gat ttg gca gtg atc gta tgt aag    1353
Gln Glu Arg His Ile Phe Leu Phe Asp Leu Ala Val Ile Val Cys Lys
        420                 425                 430 aga aaa ggt gat aac tat gaa atg aag gaa ata ata gat ctt cag cag    1401
Arg Lys Gly Asp Asn Tyr Glu Met Lys Glu Ile Ile Asp Leu Gln Gln
    435                 440                 445 tac aag ata gcc aat aat cct aca acc gat aaa gaa aac aaa aag tgg    1449
Tyr Lys Ile Ala Asn Asn Pro Thr Thr Asp Lys Glu Asn Lys Lys Trp
450                 455                 460                 465 tct tat ggc ttc tac ctc atc cat acc caa gga caa aat ggg tta gaa    1497
Ser Tyr Gly Phe Tyr Leu Ile His Thr Gln Gly Gln Asn Gly Leu Glu
                470                 475                 480 ttt tat tgc aaa aca aaa gat tta aag aag aaa tgg cta gaa cag ttt    1545
Phe Tyr Cys Lys Thr Lys Asp Leu Lys Lys Lys Trp Leu Glu Gln Phe
                485                 490                 495 gaa atg gct ttg tct aac ata aga cca gac tat gca gac tcc aat ttc    1593
Glu Met Ala Leu Ser Asn Ile Arg Pro Asp Tyr Ala Asp Ser Asn Phe
        500                 505                 510 cac gac ttc aag atg cat acc ttc act cga gtc aca tcc tgc aaa gtc    1641
His Asp Phe Lys Met His Thr Phe Thr Arg Val Thr Ser Cys Lys Val
    515                 520                 525 tgc cag atg ctc ctg agg gga aca ttt tat caa ggc tat tta tgt ttt    1689
Cys Gln Met Leu Leu Arg Gly Thr Phe Tyr Gln Gly Tyr Leu Cys Phe
530                 535                 540                 545 aag tgt gga gcg aga gca cac aaa gaa tgt ttg gga aga gta gac aat    1737
Lys Cys Gly Ala Arg Ala His Lys Glu Cys Leu Gly Arg Val Asp Asn
                550                 555                 560 tgt gcc aga gtt aat tct ggt gaa caa ggg aca ctc aaa cta cca gag    1785
Cys Gly Arg Val Asn Ser Gly Glu Gln Gly Thr Leu Lys Leu Pro Glu
                565                 570                 575 aaa cgg acc aat gga ctg cga aga act cct aaa cag gtg gat cca ggt    1833
Lys Arg Thr Asn Gly Leu Arg Arg Thr Pro Lys Gln Val Asp Pro Gly
        580                 585                 590 tta cca aag atg cag gtc att agg aac tat tct gga aca cca ccc cca    1881
Leu Pro Lys Met Gln Val Ile Arg Asn Tyr Ser Gly Thr Pro Pro Pro
595                 600                 605 gct ctg cat gaa gga ccc cct tta cag ctc cag gcc ggg gat acc gtt    1929
Ala Leu His Glu Gly Pro Pro Leu Gln Leu Gln Ala Gly Asp Thr Val
610                 615                 620                 625 gaa ctt ctg aaa gga gat gca cac agt ctg ttt tgg cag ggc aga aat    1977
Glu Leu Leu Lys Gly Asp Ala His Ser Leu Phe Trp Gln Gly Arg Asn
                630                 635                 640 tta gca tct gga gag gtt gga ttt ttt cca agt gat gca gtc aag cct    2025
Leu Ala Ser Gly Glu Val Gly Phe Phe Pro Ser Asp Ala Val Lys Pro
                645                 650                 655 tgc cca tgt gtg ccc aaa cca gta gat tat tct tgc caa ccc tgg tat    2073
Cys Pro Cys Val Pro Lys Pro Val Asp Tyr Ser Cys Gln Pro Trp Tyr
660                 665                 670
```

```
gct gga gca atg gaa aga ttg caa gca gag acc gaa ctt att aat agg    2121
Ala Gly Ala Met Glu Arg Leu Gln Ala Glu Thr Glu Leu Ile Asn Arg
675                 680                 685 gta aat agt act tac ctt gtg agg cac agg acc aaa gag tca gga gaa    2169
Val Asn Ser Thr Tyr Leu Val Arg His Arg Thr Lys Glu Ser Gly Glu
690                 695                 700                 705 tat gca att agc att aag tac aat aat gaa gca aag cac atc aag att    2217
Tyr Ala Ile Ser Ile Lys Tyr Asn Asn Glu Ala Lys His Ile Lys Ile
            710                 715                 720 tta aca aga gat ggc ttt ttt cac att gca gaa aat aga aaa ttt aaa    2265
Leu Thr Arg Asp Gly Phe Phe His Ile Ala Glu Asn Arg Lys Phe Lys
            725                 730                 735 agt tta atg gaa ctt gtg gag tac tac aag cat cat tct ctc aag gaa    2313
Ser Leu Met Glu Leu Val Glu Tyr Tyr Lys His His Ser Leu Lys Glu
            740                 745                 750 ggg ttc aga acc tta gat aca act ctg cag ttt cca tac aag gag cca    2361
Gly Phe Arg Thr Leu Asp Thr Thr Leu Gln Phe Pro Tyr Lys Glu Pro
755                 760                 765 gaa cat tca gct gga cag agg ggt aat aga gca ggc aac agc ttg tta    2409
Glu His Ser Ala Gly Gln Arg Gly Asn Arg Ala Gly Asn Ser Leu Leu
770                 775                 780                 785 agt cca aaa gtg ctg ggc att gcc atc gct cgg tat gac ttc tgt gca    2457
Ser Pro Lys Val Leu Gly Ile Ala Ile Ala Arg Tyr Asp Phe Cys Ala
            790                 795                 800 aga gat atg aga gag ttg tcc ttg ttg aaa gga gat gtg gtg aag att    2505
Arg Asp Met Arg Glu Leu Ser Leu Leu Lys Gly Asp Val Val Lys Ile
            805                 810                 815 tac aca aag atg agt gca aat ggc tgg tgg aga gga gaa gta aat ggc    2553
Tyr Thr Lys Met Ser Ala Asn Gly Trp Trp Arg Gly Glu Val Asn Gly
820                 825                 830 agg gtg ggc tgg ttt cca tcc aca tat gtg gaa gag gat gaa taa       2598
Arg Val Gly Trp Phe Pro Ser Thr Tyr Val Glu Glu Asp Glu
835                 840                 845 attcaaatcc cgtgttgcac cctgcaccaa aaatttcaga gaagggataa atagaagcct    2658
gcacagcatc gtgaattaac tgaagtgttt aaaaagctgc atttctggct gttcaacatc    2718
ctccctcctt agcccctcct aagtcttaat gctgagattt ctaaagatgc tggtactgac    2778
agattaatgg cttgcctaga gctgtgcaag aaacagcctg ccagtctgtc attgtcaggg    2838
accagggcaa aaccaagagc tgttcttccc agaagagccc tgcaaacaca ttggttcgtg    2898
cttcccttta cttcttctgg tcagatacca tgaatgccag tcatcagtaa atcttaatac    2958
acttttgctt tattctcaca tgccattcac cagattattt gatggtacaa agaagcagaa    3018
gtgtaatttt ccttttccca gcatgacgaa aaattggagt tctgccattt gagcagctta    3078
ctggaaagat ccagccttac ttgtcttaaa ttgtccaaca aggtgactca ttgcccggca    3138
aacactttta ccctcagatg ttactcatga tattataaaa tatgaggcca gtgctcaggt    3198
ttgcatcata agtgagctat ccctgaaggg ttttaattac ttatttggtg tcctgattat    3258
atttgcaaac ttctttataa aaggtgaaaa agcacacaca aagagagggt gtcttcatat    3318
taaaccttca caaccttcat gatttcatag gattattttg gaaatatagc acttgacttt    3378
atgaaaggat ctgggctagg tatattaagg gtagttgcca ataacctgaa gaagctggca    3438
ttgtttacag aaacagatca agggctataa tttatgtcat tttatagcag cagtatctat    3498
taatacatgc cttttcctcc catccacctc ccccgcacac acacaaagat gacctgggac    3558 atgattttt tattcccaca ttttcttgga gcacaaacaa ctttgttgag gattttggaa     3618
ggaaagcaca actgggtcct ttattcattt ctgggacaga aagagggtca gtggactttt    3678
```

| | |
|---|---|
| gtgggcctcc agcttctctc agagtctccc cctctgcagc ccatcctggg agtgtattaa | 3738 |
| ctggagggaa gatgggtctt gcagtacatt tgttttgccc agccatcact ctttttgtg | 3798 |
| aggagcctaa atacattctt cctggggtcc agagtcccca ttcaaggcag tcaagttaag | 3858 |
| acactaactt ggcccttttcc tgatggaaat atttcctcca tagcagaagt tgtgttctga | 3918 |
| caagactgag agagttacat gttgggaaaa aaaagaagca ttaacttagt agaactgaac | 3978 |
| caggagcatt aagttctgaa attttgaatc atctctgaaa tgaagcaggt gtagcctgcc | 4038 |
| ctctcatcaa tccgtctggg tgccagaact caaggttcag tggacacatc ccctgttag | 4098 |
| agaccctcat gggctaggac ttttcatcta ggatagattc aagacctttta cctcagaatt | 4158 |
| atgtaaactg tgattgtgtt ttagaaaaat tattatttgc taaaaccatt taagtctttg | 4218 |
| tatatgtgta aatgatcaca aaatgtatt ttataaaatg ttctgtacaa taagttaca | 4278 |
| cctcaaagtg tactcttgga atggattctt tcctgtaaag tcttatctgc gactctgtct | 4338 |
| cgggaatgtt ttgtctgttg ccgtcagccg aactttgtta tggagggagc agcctcacac | 4398 |
| aagcagaaac actcctgtgg atggtattgt agcatgtatt gtttattta gtcaatagac | 4458 |
| cctctcctta taaatggtgt ttagtcttcc tgttgcattt catgggcctg ggggtttcct | 4518 |
| agcagaggat attggagccc cttttttgtga cattaccaat tacatctttg tccacgttta | 4578 |
| atactttgtt ttggaaaatt taaatgctgc agatttgtgt agagttctaa taccaaagac | 4638 |
| agaagtaaat gttttccata tactttgtct tgcctgtatg cagccctcgt gtaatacggt | 4698 |
| gaattagagt ggtatttcac tttgtattat tttgtaaata tgtcaatata ataaatagtg | 4758 |
| actaaattga taaaaaaa | 4776 |

<210> SEQ ID NO 8
<211> LENGTH: 847
<212> TYPE: PRT
<213> ORGANISM: Homo sapiens

<400> SEQUENCE: 8

```
Met Glu Pro Trp Lys Gln Cys Ala Gln Trp Leu Ile His Cys Lys Val
1               5                   10                  15

Leu Pro Thr Asn His Arg Val Thr Trp Asp Ser Ala Gln Val Phe Asp
            20                  25                  30

Leu Ala Gln Thr Leu Arg Asp Gly Val Leu Leu Cys Gln Leu Leu Asn
        35                  40                  45

Asn Leu Arg Ala His Ser Ile Asn Leu Lys Glu Ile Asn Leu Arg Pro
    50                  55                  60

Gln Met Ser Gln Phe Leu Cys Leu Lys Asn Ile Arg Thr Phe Leu Thr
65                  70                  75                  80

Ala Cys Cys Glu Thr Phe Gly Met Arg Lys Ser Glu Leu Phe Glu Ala
                85                  90                  95

Phe Asp Leu Phe Asp Val Arg Asp Phe Gly Lys Val Ile Glu Thr Leu
            100                 105                 110

Ser Arg Leu Ser Arg Thr Pro Ile Ala Leu Ala Thr Gly Ile Arg Pro
        115                 120                 125

Phe Pro Thr Glu Glu Ser Ile Asn Asp Glu Asp Ile Tyr Lys Gly Leu
    130                 135                 140

Pro Asp Leu Ile Asp Glu Thr Leu Val Glu Asp Glu Asp Leu Tyr
145                 150                 155                 160

Asp Cys Val Tyr Gly Glu Asp Glu Gly Gly Glu Val Tyr Glu Asp Leu
                165                 170                 175
```

-continued

Met Lys Ala Glu Glu Ala His Gln Pro Lys Cys Pro Glu Asn Asp Ile
                180                 185                 190
Arg Ser Cys Cys Leu Ala Glu Ile Lys Gln Thr Glu Glu Lys Tyr Thr
            195                 200                 205
Glu Thr Leu Glu Ser Ile Glu Lys Tyr Phe Met Ala Pro Leu Lys Arg
        210                 215                 220
Phe Leu Thr Ala Ala Glu Phe Asp Ser Val Phe Ile Asn Ile Pro Glu
225                 230                 235                 240
Leu Val Lys Leu His Arg Asn Leu Met Gln Glu Ile His Asp Ser Ile
                245                 250                 255
Val Asn Lys Asn Asp Gln Asn Leu Tyr Gln Val Phe Ile Asn Tyr Lys
            260                 265                 270
Glu Arg Leu Val Ile Tyr Gly Gln Tyr Cys Ser Gly Val Glu Ser Ala
        275                 280                 285
Ile Ser Ser Leu Asp Tyr Ile Ser Lys Thr Lys Glu Asp Val Lys Leu
290                 295                 300
Lys Leu Glu Glu Cys Ser Lys Arg Ala Asn Asn Gly Lys Phe Thr Leu
305                 310                 315                 320
Arg Asp Leu Leu Val Val Pro Met Gln Arg Val Leu Lys Tyr His Leu
                325                 330                 335
Leu Leu Gln Glu Leu Val Lys His Thr Thr Asp Pro Thr Glu Lys Ala
            340                 345                 350
Asn Leu Lys Leu Ala Leu Asp Ala Met Lys Asp Leu Ala Gln Tyr Val
        355                 360                 365
Asn Glu Val Lys Arg Asp Asn Glu Thr Leu Arg Glu Ile Lys Gln Phe
    370                 375                 380
Gln Leu Ser Ile Glu Asn Leu Asn Gln Pro Val Leu Leu Phe Gly Arg
385                 390                 395                 400
Pro Gln Gly Asp Gly Glu Ile Arg Ile Thr Thr Leu Asp Lys His Thr
                405                 410                 415
Lys Gln Glu Arg His Ile Phe Leu Phe Asp Leu Ala Val Ile Val Cys
            420                 425                 430
Lys Arg Lys Gly Asp Asn Tyr Glu Met Lys Glu Ile Ile Asp Leu Gln
        435                 440                 445
Gln Tyr Lys Ile Ala Asn Asn Pro Thr Thr Asp Lys Glu Asn Lys Lys
    450                 455                 460
Trp Ser Tyr Gly Phe Tyr Leu Ile His Thr Gln Gly Gln Asn Gly Leu
465                 470                 475                 480
Glu Phe Tyr Cys Lys Thr Lys Asp Leu Lys Lys Lys Trp Leu Glu Gln
                485                 490                 495
Phe Glu Met Ala Leu Ser Asn Ile Arg Pro Asp Tyr Ala Asp Ser Asn
            500                 505                 510
Phe His Asp Phe Lys Met His Thr Phe Thr Arg Val Thr Ser Cys Lys
        515                 520                 525
Val Cys Gln Met Leu Leu Arg Gly Thr Phe Tyr Gln Gly Tyr Leu Cys
    530                 535                 540
Phe Lys Cys Gly Ala Arg Ala His Lys Glu Cys Leu Gly Arg Val Asp
545                 550                 555                 560
Asn Cys Gly Arg Val Asn Ser Gly Glu Gln Gly Thr Leu Lys Leu Pro
                565                 570                 575
Glu Lys Arg Thr Asn Gly Leu Arg Arg Thr Pro Lys Gln Val Asp Pro
            580                 585                 590

```
Gly Leu Pro Lys Met Gln Val Ile Arg Asn Tyr Ser Gly Thr Pro Pro
            595                 600                 605

Pro Ala Leu His Glu Gly Pro Pro Leu Gln Leu Gln Ala Gly Asp Thr
        610                 615                 620

Val Glu Leu Leu Lys Gly Asp Ala His Ser Leu Phe Trp Gln Gly Arg
625                 630                 635                 640

Asn Leu Ala Ser Gly Glu Val Gly Phe Phe Pro Ser Asp Ala Val Lys
                645                 650                 655

Pro Cys Pro Cys Val Pro Lys Pro Val Asp Tyr Ser Cys Gln Pro Trp
                660                 665                 670

Tyr Ala Gly Ala Met Glu Arg Leu Gln Ala Glu Thr Glu Leu Ile Asn
            675                 680                 685

Arg Val Asn Ser Thr Tyr Leu Val Arg His Arg Thr Lys Glu Ser Gly
        690                 695                 700

Glu Tyr Ala Ile Ser Ile Lys Tyr Asn Asn Glu Ala Lys His Ile Lys
705                 710                 715                 720

Ile Leu Thr Arg Asp Gly Phe Phe His Ile Ala Glu Asn Arg Lys Phe
                725                 730                 735

Lys Ser Leu Met Glu Leu Val Glu Tyr Tyr Lys His His Ser Leu Lys
                740                 745                 750

Glu Gly Phe Arg Thr Leu Asp Thr Thr Leu Gln Phe Pro Tyr Lys Glu
            755                 760                 765

Pro Glu His Ser Ala Gly Gln Arg Gly Asn Arg Ala Gly Asn Ser Leu
        770                 775                 780

Leu Ser Pro Lys Val Leu Gly Ile Ala Ile Ala Arg Tyr Asp Phe Cys
785                 790                 795                 800

Ala Arg Asp Met Arg Glu Leu Ser Leu Leu Lys Gly Asp Val Val Lys
                805                 810                 815

Ile Tyr Thr Lys Met Ser Ala Asn Gly Trp Trp Arg Gly Glu Val Asn
                820                 825                 830

Gly Arg Val Gly Trp Phe Pro Ser Thr Tyr Val Glu Glu Asp Glu
            835                 840                 845
```

THERAPEUTIC AGENT FOR TUMORS IDENTIFIED BY PHOSPHORYLATION OF PROTO-ONCOGENE PROTEIN BELONGING TO VAV FAMILY

CROSS REFERENCE TO RELATED APPLICATIONS

This application is a Continuation of PCT International Application No. PCT/JP2017/038595, filed on Oct. 19, 2017, which claims priority under 35 U.S.C. 119(a) to Patent Application No. 2016-215521, filed in Japan on Nov. 2, 2016, all of which are hereby expressly incorporated by reference into the present application.

TECHNICAL FIELD

The present invention relates to a therapeutic agent for tumors identified by phosphorylation of a proto-oncogene protein belonging to the VAV family, a method for testing the efficacy of dasatinib or other form thereof in a patient who is a subject to be administered therewith, etc.

BACKGROUND ART

Dasatinib (see Non-patent Document 1 for details of the compound and Non-patent Document 2 for its clinical trial) exerts high efficacy in chronic myelogenous leukemia through inhibition of the ATP-binding site in tyrosine kinase BCR-ABL. Dasatinib also has an inhibitory effect against tyrosine kinases other than ABL, but no effort has been made to pursue clinical development based on this effect.

Angioimmunoblastic T-cell lymphoma (AITL) is an extremely intractable blood cancer and its five-year survival rate is about 20%. AITL often presents characteristic clinical features including lymph node swelling, as well as fervescence, exanthema, autoimmune disease-like alterations, hypergammaglobulinemia and so on. The inventors of the present invention have reported the genomic analysis of AITL indicating that a RHOA gene mutation (c.50G>T) causing a glycine to valine substitution at amino acid position 17 of the RHOA protein (p.G17V, hereinafter referred to as a "G17V RHOA mutation") is observed in 70% of AITL cases (Non-patent Document 3: Sakata-Yanagimoto M, et al. Nat Genet. 2014 February; 46(2):171-5). Thus, there have been demands not only for elucidating the mechanism of oncogenesis due to these genomic alterations, but also for developing targeted therapies.

PRIOR ART DOCUMENTS

Non-Patent Documents

Non-patent Document 1: Shah NP., et al., Overriding imatinib resistance with a novel ABL kinase inhibitor, Science, vol. 305, p. 399-401, 2004
Non-patent Document 2: Talpaz M, et al., N. Engl. J. Med., 2006 Jun. 15; 354(24):2531-41
Non-patent Document 3: Sakata-Yanagimoto M. et al., Nat. Genet., 2014 February; 46(2):171-5

SUMMARY OF THE INVENTION

Under these circumstances, there has been a demand for the development of pharmaceutical formulations and therapeutic methods useful in the treatment of various tumors including angioimmunoblastic T-cell lymphoma (AITL), which is an orphan disease. In particular, for the treatment of AITL, combination chemotherapy has been used conventionally, but AITL is often refractory to conventional therapy: and hence the development of novel therapeutic agents and therapeutic methods has been awaited.

The present invention has been made in consideration of the above situation and aims to provide a therapeutic agent for tumors identified by phosphorylation of a proto-oncogene protein belonging to the VAV family, a pharmaceutical composition for the treatment of these tumors, the use of dasatinib or other form thereof for the manufacture of a pharmaceutical agent for the treatment of these tumors, a therapeutic method for these tumors, and a therapeutic kit for these rumors, as well as a method for testing the efficacy of dasatinib or other form thereof in a patient who is a subject to be administered therewith, etc., as shown below.

(1) A therapeutic agent for a tumor identified by phosphorylation of a proto-oncogene protein belonging to the VAV family,
  wherein the therapeutic agent comprises dasatinib or a prodrug thereof or a pharmacologically acceptable salt thereof or a hydrate or solvate thereof as an active ingredient.
(2) The therapeutic agent according to (1) above, wherein the tumor is a tumor identified to show enhanced phosphorylation of a proto-oncogene protein belonging to the VAV family.
(3) The therapeutic agent according to (1) or (2) above, wherein the protein is the VAV1 protein.
(4) A therapeutic agent for a tumor carrying a gene mutation or gene fusion in the RHOA gene and/or in a proto-oncogene belonging to the VAV family,
  wherein the therapeutic agent comprises dasatinib or a prodrug thereof or a pharmacologically acceptable salt thereof or a hydrate or solvate thereof as an active ingredient.
(5) The therapeutic agent according to any one of (1) to (4) above, wherein the tumor is at least one selected from the group consisting of T-cell lymphoma, gastric cancer, pancreatic cancer, skin tumor, colorectal cancer, uterine cancer and nervous system tumor.
(6) The therapeutic agent according to any one of (1) to (5) above, wherein the tumor is T-cell lymphoma.
(7) The therapeutic agent according to any one of (1) to (6) above, wherein the T-cell lymphoma is angioimmunoblastic T-cell lymphoma or peripheral T-cell lymphoma, not otherwise specified.
(8) A pharmaceutical composition for the treatment of a tumor identified by phosphorylation of a proto-oncogene protein belonging to the VAV family, which comprises dasatinib or a prodrug thereof or a pharmacologically acceptable salt thereof or a hydrate or solvate thereof.

The present invention also encompasses a pharmaceutical composition for the treatment of a tumor carrying a gene mutation or gene fusion in the RHOA gene and/or in a proto-oncogene belonging to the VAV family, which comprises dasatinib or a prodrug thereof or a pharmacologically acceptable salt thereof or a hydrate or solvate thereof.

(9) The use of dasatinib or a prodrug thereof or a pharmacologically acceptable salt thereof or a hydrate or solvate thereof for the manufacture of a pharmaceutical agent for the treatment of a tumor identified by phosphorylation of a proto-oncogene protein belonging to the VAV family.

The present invention also encompasses the use of dasatinib or a prodrug thereof or a pharmacologically acceptable salt thereof or a hydrate or solvate thereof for the manufacture of a pharmaceutical agent for the treatment of a tumor carrying a gene mutation or gene fusion in the RHOA gene and/or in a proto-oncogene belonging to the VAV family.

(10) A therapeutic method for a tumor identified by phosphorylation of a proto-oncogene protein belonging to the VAV family, which comprises administering a subject with dasatinib or a prodrug thereof or a pharmacologically acceptable salt thereof or a hydrate or solvate thereof.

The present invention also encompasses a therapeutic method for a tumor carrying a gene mutation or gene fusion in the RHOA gene and/or in a proto-oncogene belonging to the VAV family, which comprises administering a subject with dasatinib or a prodrug thereof or a pharmacologically acceptable salt thereof or a hydrate or solvate thereof.

(11) A therapeutic kit for a tumor identified by phosphorylation of a proto-oncogene protein belonging to the VAV family, which comprises dasatinib or a prodrug thereof or a pharmacologically acceptable salt thereof or a hydrate or solvate thereof.

The present invention also encompasses a therapeutic kit for a tumor carrying a gene mutation or gene fusion in the RHOA gene and/or in a proto-oncogene belonging to the VAV family, which comprises dasatinib or a prodrug thereof or a pharmacologically acceptable salt thereof or a hydrate or solvate thereof.

(12) A method for testing the efficacy of dasatinib or a prodrug thereof or a pharmacologically acceptable salt thereof or a hydrate or solvate thereof in a patient who is a subject to be administered therewith, wherein the efficacy is indicated by the level of phosphorylation of a proto-oncogene protein belonging to the VAV family in an analyte taken from the patient.

(13) A method for testing the efficacy of dasatinib or a prodrug thereof or a pharmacologically acceptable salt thereof or a hydrate or solvate thereof in a patient who is a subject to be administered therewith, wherein the efficacy is indicated by the presence or absence of a gene mutation or gene fusion in the RHOA gene in an analyte taken from the patient.

(14) A method for testing the efficacy of dasatinib or a prodrug thereof or a pharmacologically acceptable salt thereof or a hydrate or solvate thereof in a patient who is a subject to be administered therewith, wherein the efficacy is indicated by the presence or absence of a gene mutation or gene fusion in the VAV1 gene in an analyte taken from the patient.

(15) A method for testing the efficacy of dasatinib or a prodrug thereof or a pharmacologically acceptable salt thereof or a hydrate or solvate thereof in a patient who is a subject to be administered therewith, wherein the efficacy is indicated by the presence or absence of a gene mutation or gene fusion in the VAV2 gene in an analyte taken from the patient.

(16) A method for testing the efficacy of dasatinib or a prodrug thereof or a pharmacologically acceptable salt thereof or a hydrate or solvate thereof in a patient who is a subject to be administered therewith, wherein the efficacy is indicated by the presence or absence of a gene mutation or gene fusion in the VAV3 gene in an analyte taken from the patient.

Effects of the Invention

The present invention enables the provision of a pharmaceutical formulation and a pharmaceutical composition, each being useful in the treatment of tumors identified by phosphorylation of a proto-oncogene protein belonging to the VAV family, a method useful in the treatment of these tumors, and a therapeutic kit for these tumors, etc. Particularly in the treatment of intractable diseases such as angioimmunoblastic T-cell lymphoma (AITL), dasatinib can be expected to produce a more specific and efficacious therapeutic effect because dasatinib inhibits the activation of VAV protein molecules, per se, which are activated by a mutation or the like in the RHOA gene and/or in a proto-oncogene belonging to the VAV family.

Moreover, the present invention also enables the provision of a method for testing the efficacy of dasatinib or other form thereof in a patient who is a subject to be administered therewith.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 7(A) indicates that in Jurkat cells, dasatinib cancels the enhanced Y174 phosphorylation induced by G17V RHOA mutant expression.

FIG. 7(B) indicates that in Jurkat cells, dasatinib cancels the enhanced PLC-gamma 1 phosphorylation induced by G17V RHOA mutant expression.

DESCRIPTION OF EMBODIMENTS

Figure 1:
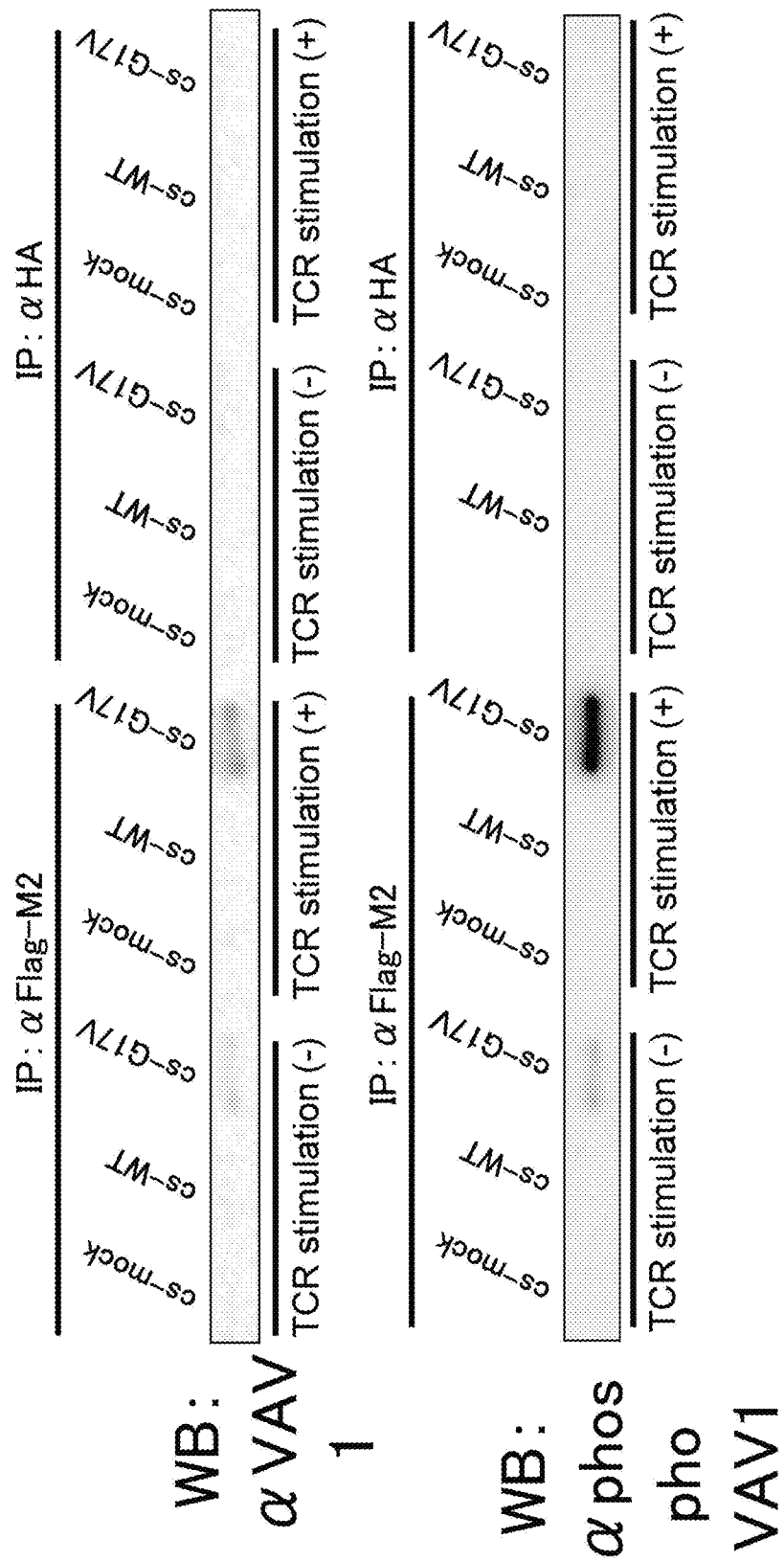
FIG. 1 indicates that in acute T-cell leukemia cell line Jurkat cells, a G17V RHOA mutant binds to VAV1, which is a molecule important for T cell receptor (TCR) signaling.

The present invention will be further described in more detail below. The scope of the present invention is not limited by the following description, and any embodiments other than those illustrated below may also be carried out with appropriate modifications without departing from the spirit of the present invention. It should be noted that this specification incorporates the specification of Japanese Patent Application No. 2016-215521 (filed on Nov. 2, 2016) in its entirety, based on which the present application claims priority. Moreover, all publications cited herein, including prior art documents, patent gazettes and other patent documents, are incorporated herein by reference.

1. Overview of the Present Invention

Proto-oncogene proteins belonging to the VAV family, such as VAV1, are molecules critically important for T cell receptor signaling and are known to be activated upon phosphorylation by Src family kinases. The inventors of the present invention have found that a G17V RHOA mutant binds to VAV1 and enhances the phosphorylation (tyrosine phosphorylation) thereof to thereby activate the downstream signaling of VAV1, and that in some cases with no G17V RHOA mutation, a gene mutation is found in VAV1 per se and this mutation causes VAV1 activation. The inventors of the present invention have further found that VAV1 activation (abnormal activation) caused by such a G17ITV RHOA mutant or VAV1 mutant is inhibited by dasatinib. Moreover, the inventors of the present invention have found that the NFAT activity-enhancing effect of the VAV1 mutant under T cell receptor signaling is inhibited by dasatinib, and further that interleukin-2 (IL-2) production by the G17V RHOA mutant under T cell receptor signaling is inhibited by dasatinib.

Based on these findings, the inventors of the present invention have found out the present invention directed to a therapeutic agent for AITL comprising dasatinib, more particularly a therapeutic agent for tumors identified by phosphorylation (tyrosine phosphorylation) of a proto-oncogene protein belonging to the VAV family, etc.

2. Therapeutic Agent, Pharmaceutical Composition and Others for Tumor Treatment The therapeutic agent of the present invention for a tumor identified by phosphorylation of a proto-oncogene protein belonging to the VAV family (hereinafter also simply referred to as "the therapeutic agent of the present invention") and the pharmaceutical composition of the present invention for the treatment of a tumor identified by phosphorylation of a proto-oncogene protein belonging to the VAV family (hereinafter also simply referred to as "the pharmaceutical composition of the present invention") are each characterized by comprising dasatinib or a prodrug thereof or a pharmacologically acceptable salt thereof or a hydrate or solvate thereof (hereinafter also referred to as "dasatinib or other form thereof") as an active ingredient, as described above.

It should be noted that the present invention also encompasses: (i) a therapeutic method for a tumor identified by phosphorylation of a proto-oncogene protein belonging to the VAV family, which comprises using dasatinib or other form thereof, e.g., more specifically administering an effective amount of dasatinib or other form thereof to a subject (i.e., a patient with a tumor identified by phosphorylation of a proto-oncogene protein belonging to the VAV family or a patient at the risk thereof, or alternatively, such a non-human mammal); (ii) the use of dasatinib or other form thereof for the manufacture of a pharmaceutical agent for the treatment of such a tumor; (iii) the use of dasatinib or other form thereof for the treatment of such a tumor; and (iv) dasatinib or other form thereof for use in the treatment of such a tumor.

In the present invention, the treatment of such a tumor more specifically also includes, for example, suppression of tumor progression, improvement of prognosis, and/or prevention of recurrence, etc.

In the present invention, the tumor to be treated is a tumor identified by phosphorylation (tyrosine phosphorylation) of a proto-oncogene protein belonging to the VAV family. As intended herein, the tumor identified by phosphorylation of such a protein is not limited in any way and may be, for example, a tumor in a state identified to show enhanced (or improved) phosphorylation of the protein when compared to that in the tissue of normal subjects. Moreover, in the present invention, other tumors to be treated are preferably exemplified by tumors carrying a gene mutation or gene fusion in the RHOA gene and/or in a proto-oncogene belonging to the VAV family. More specifically, these tumors to be treated are preferably exemplified by T-cell lymphoma (preferably angioimmunoblastic T-cell lymphoma (AITL), peripheral T-cell lymphoma, not otherwise specified, etc.), gastric cancer, pancreatic cancer, skin tumor, colorectal cancer, uterine cancer, and nervous system tumor, etc.

Examples of a proto-oncogene protein belonging to the VAV family include VAV1, VAV2 and VAV3. In particular, in the case of VAV1, its activation induced by phosphorylation (abnormal activation induced by enhanced tyrosine phosphorylation) is a factor responsible for causing T-cell lymphoma, particularly angioimmunoblastic T-cell lymphoma (AITL).

In the present invention, examples of a gene mutation in the RHOA gene (SEQ ID NO: 1 (NCBI GenBank Accession No. NM_001664.3): cDNA covers nucleotides at positions 281 to 862 among 1943 nucleotides) include, but are not limited to, those shown in Table 1 below, including a gene (DNA) mutation (c.50G>T) which results in an amino acid mutation p.G17V (G17V RHOA mutation) in the RHOA protein (SEQ ID NO: 2). Further examples include gene mutations resulting in amino acid mutations p.A161E, p.A161P, p.A161V and p.A118E in this protein.

As to the notation of gene mutations used herein, for example, "c.50G>T" refers to a G to T substitution at nucleotide position 50 of cDNA, and "c.C518_529del" refers to C deletions at positions 518 and 529 of cDNA.

Likewise, as to the notation of amino acid mutations in the protein, for example, "p.G17V" refers to a G (glycine) to V (valine) substitution at position 17 of the amino acid sequence encoded by cDNA. "p.E175V/L" refers to a E (glutamic acid) to V (valine) or L (leucine) substitution at position 175 of the amino acid sequence, "p.173_177del" refers to deletion of residues at positions 173 and 177 of the amino acid sequence, and "p.R24*" refers to a mutation where the codon encoding R (arginine) at position 24 of the amino acid sequence is converted into a stop codon.

TABLE 1

| RHOA gene mutation | Amino acid mutation in RHOA protein |
|---|---|
| c.50G > T | p.G17V |
| c.125A > G | p.Y42C |
| c.46T > C | p.C16R |
| c.14G > A | p.R5Q |
| c.14G > A | p.G17E |

Moreover, in the present invention, examples of a gene mutation in a proto-oncogene belonging to the VAV family include, but are not limited to, gene mutations in the VAV1 gene (SEQ ID NO: 3 (NCBI GenBank Accession No. NM_005428.3): cDNA covers nucleotides at positions 141 to 2678 among 2944 nucleotides), which result in amino acid mutations in the VAV1 protein (SEQ ID NO: 4) as shown in Table 2 below. Further examples include gene mutations resulting in amino acid mutations p.E157K, p.Y174C, p.E175V/L, p.L177R, p.K494R, p.Q487K/R, p.M501R/L/V, p.E556K, p.P615L, p.R790C, p.D797N/H, p.R798P, p.J815SE and p.R822L in this protein.

TABLE 2

| VAV1 gene mutation | Amino acid mutation in VAV1 protein |
|---|---|
| c.C518_529del | p.173_177del |
| c.C494_520del | p.165_174del |
| c.1668G > C | p.E556D |
| c.1844C > T | p.P615L |
| c.1211A > G | p.K404R |
| c.2465G > A | p.R822Q |
| c.388C > T | p.P130S |
| c.2393G > A | p.R798Q |
| c.1696C > T | p.R566* |

Likewise, in the case of the VAV2 gene (SEQ ID NO: 5 (NCBI GenBank Accession No. NM_001134398.1): cDNA covers nucleotides at positions 47 to 2683 among 4865 nucleotide), examples include gene mutations resulting in amino acid mutations in the VAV2 protein (SEQ ID NO: 6) as shown in Table 3 below. Further examples include gene mutations resulting in amino acid mutations p.R103Q, p.R76H, p.D760N, p.G854D, p.P657S, p.L88F, p.D170E/G, p.R700Q, p.A362T and p.P130L in this protein.

TABLE 3

| VAV2 gene mutation | Amino acid mutation in VAV2 protein |
|---|---|
| c.763C > T | p.L255L |
| c.748C > T | p.L250L |
| c.686C > T | p.P229L |
| c.701C > T | p.P234L |
| c.308G > A | p.R103Q |

Likewise, in the case of the VAV3 gene (SEQ ID NO: 7 (NCBI GenBank Accession No. NM_0.006113.4): cDNA covers nucleotides at positions 55 to 2598 among 4776 nucleotides), examples include gene mutations resulting in amino acid mutations in the VAV3 protein (SEQ ID NO: 8) as shown in Table 4 below. Further examples include gene mutations resulting in amino acid mutations p.R24*, p.V275M, p.A213T, p.E53D, p.V65I, p.W277*, C98*, p.L198*, p.K187*, p.W112 and p.G79fs in this protein. As used here, "p.G79fs" refers to a frameshift mutation where the codon encoding G (glycine) at position 79 of the amino acid sequence is translated as another codon.

TABLE 4

| VAV3 gene mutation | Amino acid mutation in VAV3 protein |
|---|---|
| c.1309G > A | p.D437N |
| c.1037C > T | p.T346I |
| c.578G > A | p.R193Q |
| c.2382C > T | p.I794I |

Moreover, in the present invention, examples of a gene fusion in a proto-oncogene belonging to the VAV family include, but are not limited to, VAV1-STAP2, VAV1-GSS, VAV1-MYO1F and so on in the case of the VAV1 gene.

Dasatinib for use as an active ingredient in the therapeutic agent or pharmaceutical composition of the present invention may be a known commercially available product, but is not limited thereto, and may also be synthesized, extracted and purified independently for this purpose.

It should be noted that dasatinib is officially known as N-(2-chloro-6-methyl-phenyl)-2-[[6-[4-(2-hydroxyethyl)-1-piperazinyl]-2-methyl-4-pyrimidinyl]amino]-5-thiazolecarboxamide and is represented by the following structural formula.

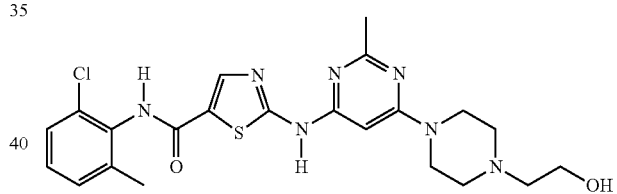

As an active ingredient in the therapeutic agent or pharmaceutical composition of the present invention, a dasatinib derivative may also be used in combination with dasatinib or in place of dasatinib. Such a derivative is not limited in any way as long as it is considered to be a derivative of dasatinib on the basis of common knowledge shared among those skilled in the art, e.g., in terms of having a chemical structure derived from dasatinib, and preferred is a derivative having the ability to suppress the phosphorylation-induced activation of a proto-oncogene protein belonging to the VAV family (e.g., VAV1) at the same level as dasatinib.

Examples of dasatinib or a derivative thereof for use in the present invention include not only those which undergo in vivo metabolism such as oxidation, reduction, hydrolysis or conjugation, but also compounds which produce dasatinib or derivatives thereof upon in vivo metabolism such as oxidation, reduction or hydrolysis (i.e., so-called prodrugs). In the present invention, such a prodrug refers to a compound prepared by modifying its parent compound with a pharmacologically acceptable group commonly used in prodrugs, and is exemplified by a compound which is provided with properties such as improved stability and sustainability and can be expected to exert the intended effect when converted into the parent compound in the intestinal tract or elsewhere.

For example, a prodrug of a compound such as dasatinib can be prepared in a standard manner by using a prodrug-forming reagent such as a corresponding halide to introduce a prodrug-constituting group(s) as appropriate in a standard manner into any one or more groups selected from among the groups in this compound, which can be used for prodrug formation (e.g., a hydroxyl group, an amino group, other groups), optionally followed by isolation and purification. As intended here, the above prodrug-constituting groups preferably include, but are not limited to, lower alkyl-CO—, lower alkyl-O-lower alkylene-CO—, lower alkyl-OCO-lower alkylene-CO—, lower alkyl-OCO—, and lower alkyl-O-lower alkylene-OCO—, etc.

As an active ingredient in the therapeutic agent or pharmaceutical composition of the present invention, a pharmacologically acceptable salt of dasatinib or a dasatinib derivative or a prodrug thereof may also be used in combination with dasatinib or a dasatinib derivative or a prodrug thereof or in place of dasatinib or a dasatinib derivative or a prodrug thereof.

Examples of a pharmacologically acceptable salt of dasatinib or a derivative thereof preferably include, but are not limited to, halogenated hydroacid salts (e.g., hydrochloride salt, hydrobromide salt, and hydroiodide salt), inorganic acid salts (e.g., sulfate salt, nitrate salt, perchlorate salt, phosphate salt, carbonate salt, and bicarbonate salt), organic carboxylic acid salts (e.g., acetate salt, trifluoroacetate salt, maleate salt, tartrate salt, fumarate salt, and citrate salt), organic sulfonic acid salts (e.g., methanesulfonate salt, trifluoromethanesulfonate salt, ethanesulfonate salt, benzenesulfonate salt, toluenesulfonate salt, and camphorsulfonate salt), amino acid salts (e.g., aspartate salt, and glutamate salt), quaternary amine salts, alkali metal salts (e.g., sodium salt, and potassium salt), alkaline earth metal salts (e.g., magnesium salt, and calcium salt), etc.

Dasatinib or other form thereof for use in the present invention includes all isomers possible in terms of the compound's structure (e.g., geometrical isomers, optical isomers based on asymmetric carbons, rotational isomers, stereoisomers, and tautomers) and mixtures of two or more of these isomers, and is not limited to the descriptions about the structural formula shown for convenience' sake. Moreover, dasatinib or other form thereof may be in S-configuration, R-configuration or RS-configuration, and is not limited in any way. Further, dasatinib or other form thereof may be present in the form of a hydrate or solvate, depending on its type. In the present invention, such a hydrate or solvate also falls within dasatinib or other form thereof, and may be used as an active ingredient in the therapeutic agent or pharmaceutical composition of the present invention. Examples of such a solvate include, but are not limited to, a solvate with ethanol, etc.

In the therapeutic agent or pharmaceutical composition of the present invention, the content of dasatinib or other form thereof as an active ingredient is not limited in any way and may be set as appropriate, for example, to be within the range of 0.01% to 99% by weight relative to the total amount of the therapeutic agent or pharmaceutical composition, and preferably to be within the range of 0.01% to 30% by weight, more preferably 0.05% to 20% by weight, and even more preferably 0.1% to 10% by weight. When the active ingredient content is within the above range, the therapeutic agent or pharmaceutical composition of the present invention will be able to suppress the phosphorylation-induced activation of a proto-oncogene protein belonging to the VAV family (e.g., VAV1) and thus exert a sufficient therapeutic effect on tumors identified by this phosphorylation.

The therapeutic agent or pharmaceutical composition of the present invention may further comprise other ingredients in addition to dasatinib or other form thereof, as long as the effect of the present invention is not significantly impaired. For example, in the present invention, dasatinib or other form thereof may be used in combination with one or more pharmaceutical agents which are known as therapeutic agents for T-cell lymphoma or under development for this purpose, as exemplified by prednisolone, dexamethasone, cyclophosphamide, doxorubicin, vincristine, azacytidine, poteligeo, romidepsin, adcetris, pralatrexate and so on, without being limited thereto. Further, the therapeutic agent or pharmaceutical composition of the present invention may comprise, for example, ingredients commonly used in pharmaceutical production as described later, etc.

The therapeutic agent or pharmaceutical composition of the present invention may be administered to a human or non-human mammalian subject (e.g., rat, rabbit, sheep, pig, cattle, cat, dog, monkey) by various routes of administration, as specifically exemplified by oral administration or parenteral administration (e.g., intravenous injection, intramuscular injection, intraperitoneal injection, subcutaneous injection, intrarectal administration, percutaneous administration). Thus, dasatinib or other form thereof for use in the present invention may be not only used alone, but also formulated with a pharmaceutically acceptable carrier into an appropriate dosage form in a manner commonly used, depending on the intended route of administration.

Dosage forms for oral formulations may be exemplified by tablets, powders, fine granules, granules, coated tablets, capsules, solutions for internal use, suspensions, emulsions, syrups and troches, etc., while dosage forms for parenteral formulations may be exemplified by injections (including drops), inhalants, ointments, nose drops, and liposomes, etc. It should be noted that when formulated into various oral formulations mentioned above, the therapeutic agent or pharmaceutical composition of the present invention may also be used as supplements (e.g., corresponding to functional food products) in some cases.

Examples of carriers which may be used to formulate these formulations include commonly used excipients, binders, disintegrants, lubricants, colorants, and correctives, as well as optionally stabilizers, emulsifiers, absorbefacients, surfactants, pH adjusters, antiseptics, antioxidants, extenders, humectants, surface active agents, dispersants, buffering agents, preservatives, solvent aids, and soothing agents, etc., which may be blended with known ingredients available for use as source materials for pharmaceutical formulations and then formulated in a standard manner.

Non-toxic ingredients available for this purpose may be exemplified by animal and vegetable oils including soybean oil, beef tallow, and synthetic glycerides; hydrocarbons including liquid paraffin, squalane, and hard paraffin; ester oils including octyldodecyl myristate, and isopropyl myristate; higher alcohols including cetostearyl alcohol, and behenyl alcohol; silicone resin: silicone oil; surfactants including polyoxyethylene fatty acid esters, sorbitan fatty acid esters, glycerin fatty acid esters, polyoxyethylenesorbitan fatty acid esters, polyoxyethylene hydrogenated castor oil, and polyoxyethylene-polyoxypropylene block copolymers; water-soluble polymers including hydroxyethylcellulose, polyacrylic acid, carboxyvinyl polymers, polyethylene glycol, polyvinylpyrrolidone, and methylcellulose; lower alcohols including ethanol, and isopropanol; polyhydric alcohols (polyols) including glycerin, propylene glycol, dipropylene glycol, sorbitol, and polyethylene glycol: sugars including glucose, and sucrose; inorganic powders including silicic anhydride, magnesium aluminum silicate, and aluminum silicate; inorganic salts including sodium chloride, and sodium phosphate: purified water, etc., and these ingredients may be in salt or hydrate form.

Preferred examples of excipients include lactose, fructose, corn starch, sucrose, glucose, mannitol, sorbit, crystalline cellulose, and silicon dioxide. Preferred examples of binders include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, polypropylene glycol-polyoxyethylene block polymers, and meglumine. Preferred examples of disintegrants include starch, agar, gelatin powder, crystalline cellulose, calcium carbonate, sodium bicarbonate, calcium citrate, dextrin, pectin, and carboxymethylcellulose calcium. Preferred examples of lubricants include magnesium stearate, talc, polyethylene glycol, silica, and hydrogenated vegetable oils. Preferred examples of colorants include those approved for addition to pharmaceutical products. Preferred examples of correctives include cocoa powder, menthol, aromatic powder, peppermint oil, borneol, and cinnamon powder. These ingredients may be in salt or hydrate form.

The dose of the therapeutic agent or pharmaceutical composition of the present invention may generally be determined extensively as appropriate for the age and body weight of a subject (patient) to be administered, the type and progression of disease, the route of administration, the frequency of administration (per day), the period of administration, etc., in consideration of the ratio of the active ingredient (dasatinib or other form thereof) incorporated into the formulation.

A detailed explanation will be given below for the case where the therapeutic agent or pharmaceutical composition of the present invention is used as a parenteral formulation or as an oral formulation.

For use as a parenteral formulation, the therapeutic agent or pharmaceutical composition of the present invention may usually be formulated into any dosage form. In the case of various types of injections, for example, they may be provided in the form of unit dose ampules or multi-dose containers or as freeze-dried powders which are dissolved again in a diluent before use. Such a parenteral formulation may comprise not only dasatinib or other form thereof serving as an active ingredient, but also various known excipients and/or additives as appropriate for each dosage form as long as the effect of the above active ingredient is not impaired. In the case of various types of injections, examples of excipients and/or additives include water, glycerol, propylene glycol, and aliphatic polyalcohols such as polyethylene glycol, etc.

The dose (daily dose) of such a parenteral formulation is not limited in any way. For example in the case of various types of injections, the dose may generally be set such that dasatinib or other form thereof serving as an active ingredient can be taken in an amount of 0.01 to 1000 mg, 0.05 to 500 mg or 0.1 to 50 mg, per kg body weight of a subject to be applied (e.g., a subject, a patient), or alternatively, can be taken in an amount of 0.5 to 20 mg or can be taken in an amount of 1 to 10 mg.

For use as an oral formulation, the therapeutic agent or pharmaceutical composition of the present invention may usually be formulated into any dosage form among those mentioned above, or alternatively, may be formulated into a freeze-dried product which is dissolved again before use. Such an oral formulation may comprise not only dasatinib or other form thereof serving as an active ingredient, but also various known excipients and/or additives as appropriate for each dosage form as long as the effect of the above active ingredient is not impaired. Examples of excipients and/or additives include binders (e.g., syrup, gum arabic, gelatin, sorbitol, tragacanth, polyvinylpyrrolidone), fillers (e.g., lactose, sugar, corn starch, potato starch, calcium phosphate, sorbitol, glycine), lubricants (e.g., magnesium stearate, talc, polyethylene glycol, silica), disintegrants (e.g., various types of starches), and wetting agents (e.g., sodium lauryl sulfate), etc.

The dose (daily dose) of such an oral formulation may generally be set such that dasatinib or other form thereof serving as an active ingredient can be taken in an amount of 0.05 to 5000 mg, 0.1 to 1000 mg or 0.1 to 100 mg, per kg body weight of a subject to be applied (e.g., a subject, a patient), or alternatively, can be taken in an amount of 0.5 to 50 mg or can be taken in an amount of 1 to 10 mg. Moreover, the ratio of the active ingredient incorporated into the oral formulation is not limited in any way and may be set as appropriate in consideration of the frequency of administration per day, etc.

3. Kit

In the treatment of tumors identified by phosphorylation of a proto-oncogene protein belonging to the VAV family, a kit comprising dasatinib or other form thereof can be used for this purpose (as specifically exemplified by a kit comprising the therapeutic agent or pharmaceutical composition of the present invention mentioned above).

In such a kit, dasatinib or other form thereof may be contained in any state, but may be provided, for example, in a dissolved state in consideration of its stability (storage quality) and easiness of use, etc.

Such a kit may comprise not only dasatinib or other form thereof, but also other constituent elements, as appropriate.

Such a kit is required to comprise at least the above dasatinib or other form thereof as a constituent element. Thus, the kit may be configured to comprise all constituent elements essential for the treatment of the above tumors, either together with or separately from dasatinib or other form thereof, without being limited thereto.

4. Method for Testing the Efficacy of Pharmaceutical Agent in Patient

In the present invention, there is provided a method for testing the efficacy of dasatinib or a prodrug thereof or a pharmacologically acceptable salt thereof or a hydrate or solvate thereof (dasatinib or other form thereof) in a patient who is a subject to be administered therewith (hereinafter also referred to as "the test method of the present invention"). In more detail, this method is a test method for determining (or deciding) a patient for whom the administration of dasatinib or other form thereof is effective.

It should be noted that the present invention also provides a method for determining or deciding whether the administration of dasatinib or other form thereof is effective (i.e., the efficacy of this administration) in a patient who is a subject to be administered.

Each method mentioned above does not require any judgment or diagnosis made by a physician and is intended to test or determine (or decide), in advance of administration, whether dasatinib or other form thereof has an effect (i.e., a therapeutic effect on tumors) when administered to each patient, in accordance with the procedures (i) to (iii) described later.

In each method mentioned above, the efficacy is not limited in any way, but is exemplified by the efficacy in tumor treatment.

Preferred examples of the test method of the present invention include: (i) a method characterized in that the efficacy is indicated by the level of phosphorylation of a proto-oncogene protein belonging to the VAV family (e.g., VAV1, VAV2, VAV3) in an analyte taken from the above patient; (ii) a method characterized in that the efficacy is indicated by the presence or absence of a gene mutation or gene fusion in the RHOA gene in the analyte; and (iii) a method characterized in that the efficacy is indicated by the presence or absence of a gene mutation or gene fusion in a proto-oncogene belonging to the VAV family (e.g., VAV1 gene, VAV2 gene, VAV3 gene) in the analyte.

In the above methods (i) to (iii), any analyte may be taken from a patient, but preferred examples include tumor tissues (e.g., lymph node lesions and extralymphatic lesions), serum, plasma, blood cells, pleural effusion, ascites, spinal fluid and so on.

In the case of the above method (i), the indicator of the test, i.e., the level of phosphorylation (tyrosine phosphorylation) of a proto-oncogene protein belonging to the VAV family may be measured or determined, for example, by immunohistological staining, Western blotting and other techniques. If the level of phosphorylation is positive in a certain percentage or higher of cells (e.g., 10% or higher, preferably 20% or higher, more preferably 40% or higher, based on cell counts), the patient to be administered from which the analyte was taken can be determined to be a patient for whom the administration of dasatinib or other form thereof is effective. In more detail, this determination can also be made if phosphorylated VAV1/VAV2/VAV3 can be detected by Western blotting, if cells where VAV1/VAV2/VAV3 is more strongly stained than in normal lymph nodes can be found by immunostaining, or if positively stained cells can be found at a higher percentage than in normal lymph nodes.

In the case of the above method (ii), the indicator of the test, i.e., the presence or absence of a gene mutation or gene fusion in the RHOA gene may be detected, for example, by direct sequencing, allele-specific PCR, sequencing with a next-generation sequencer, PNA-LNA PCR clamp, digital PCR, WAVE and other techniques for gene mutation detection, or by reverse transcription-polymerase chain reaction (RT-PCR), genomic PCR, chromosomal analysis, fluorescence in situ hybridization (FISH), total RNA sequencing and other techniques for gene fusion detection.

Examples of a gene mutation in the RHOA gene include, but are not limited to, those shown in Table 5 below, etc.

TABLE 5

| RHOA gene mutation | Amino acid mutation in RHOA protein |
|---|---|
| c.50G > T | p.G17V |
| c.125A > G | p.Y42C |
| c.46T > C | p.C16R |
| c.14G > A | p.R5Q |
| c.14G > A | p.G17E |

In the case of the above method (iii), the presence or absence of a gene mutation or gene fusion in a proto-oncogene belonging to the VAV family (e.g., VAV1 gene, VAV2 gene, VAV3 gene) may be detected, for example, by direct sequencing, sequencing with a next-generation sequencer, digital PCR, WAVE and other techniques for gene mutation detection, or by reverse transcription-polymerase chain reaction (RT-PCR), genomic PCR, chromosomal analysis, fluorescence in situ hybridization (FISH), total RNA sequencing and other techniques for gene fusion detection.

Examples of a gene mutation in a proto-oncogene belonging to the VAV family include, but are not limited to, those in the VAV1 gene, as exemplified by VAV1 gene mutations resulting in amino acid mutations in the VAV1 protein as shown in Table 6 below.

TABLE 6

| VAV1 gene mutation | Amino acid mutation in VAV1 protein |
|---|---|
| c.C518_529del | p.173_177del |
| c.C494_520del | p.165_174del |
| c.1668G > C | p.E556D |
| c.1844C > T | p.P615L |
| c.1211A > G | p.K404R |
| c.2465G > A | p.R822Q |
| c.388C > T | p.P130S |
| c.2393G > A | p.R798Q |
| c.1696C > T | p.R566* |

Likewise, in the case of the VAV2 gene, examples include VAV2 gene mutations resulting in amino acid mutations in the VAV2 protein as shown in Table 7 below.

TABLE 7

| VAV2 gene mutation | Amino acid mutation in VAV2 protein |
|---|---|
| c.763C > T | p.L255L |
| c.748C > T | p.L250L |
| c.686C > T | p.P229L |
| c.701C > T | p.P234L |
| c.308G > A | p.R103Q |

Likewise, in the case of the VAV3 gene, examples include VAV3 gene mutations resulting in amino acid mutations in the VAV3 protein as shown in Table 8 below.

TABLE 8

| VAV3 gene mutation | Amino acid mutation in VAV3 protein |
|---|---|
| c.1309G > A | p.D437N |
| c.1037C > T | p.T346I |
| c.578G > A | p.R193Q |
| c.2382C > T | p.I794I |

Moreover, examples of a gene fusion in a proto-oncogene belonging to the VAV family include, but are not limited to, VAV1-STAP2, VAV1-GSS and so on in the case of the VAV1 gene.

The test method of the present invention enables, in advance of treatment, the selection and determination of a patient for whom the use of dasatinib or other form thereof is highly likely to provide an effective outcome in tumor treatment. This in turn enables further reduction of therapeutic burdens (i.e., economic, time and physical burdens) in patients.

EXAMPLES

The present invention will be further described in more detail by way of the following examples, although the present invention is not limited only to these examples.

1. Data Indicating VAV1 Activation Induced by G17V RHOA Mutant (Examples 1 to 4)

Example 1

(1) Jurkat cells (T-cell leukemia cell line) engineered with a lentivirus-mediated Tet-On system to express wild-type RHOA cDNA or a RHOA coding region modified to comprise a G to T substitution at position 50 of the coding region (hereinafter referred to as G17V RHOA cDNA) were seeded in RPMI (10% FCS, 1% PS) at $2 \times 10^5$ cells/mL in 15 cm petri dishes in triplicate. Doxycycline was added to give a final concentration of 2 µg/mL. On the following day, the cells were collected and centrifuged, and then seeded in RPMI (serum-free) at $6 \times 10^5$ cells/mL in 15 cm petri dishes in triplicate. After 4 hours, the cells were collected and washed once with sterile phosphate buffered saline (PBS), and then adjusted to $2 \times 10^4$ cells/ml and transferred to 15 ml tubes, followed by incubation at 37° C. for 5 minutes. LEAF™ purified anti-human CD3 Ab (BioLegend) and anti-mouse IgG antibody Ab (at 2 µg/ml each) were added. The cells were incubated at 37° C. for 5 minutes or 30 minutes. Cold PBS (10 ml) was added to each tube, followed by centrifugation to remove the supernatants. Lysis buffer (supplemented in advance with complete protease inhibitor and PhosSTOP) was added in a volume of 1000 µl/tube. The tubes were incubated on ice for 20 minutes and centrifuged to collect the supernatants. Laemuli's buffer and DTT were added, followed by incubation at 95° C. for 5 minutes.

(2) Immunoprecipitation

The remaining supernatants were each taken in a volume of 500 µL×two tubes, to which anti-flagM2 antibody and anti-HA antibody as a control (5 µg each) were added respectively, followed by rotation at 4° C. for 2 hours. Protein G was tapped and 50 µl of which was then transferred to another tube. Protein G was washed twice with 1% triton TBS.

The tubes were centrifuged at 10000 rpm at 4° C. for 10 seconds to remove the supernatants (repeated twice). The washed 50% protein G was added in 50 µL volumes to the supernatants, followed by rotation at 4° C. for 1 hour. The tubes were centrifuged at 1700 rpm at 4° C. for 2 minutes to remove the supernatants. To the pellets, 1% Triton TBS (500 µL) was added, followed by rotation at 4° C. for 5 minutes and centrifugation at 1700 rpm at 4° C. for 2 minutes to remove the supernatants. This operation was repeated three times in total. 1×Flag peptide (diluted to 500 µg/ml with TBS) was added in 50 µL volumes, followed by rotation at room temperature for 10 minutes and centrifugation at 1700 rpm at 4° C. for 2 minutes. The supernatants were collected, and Laemulis buffer and DTT were added thereto, followed by incubation at 95° C. for 5 minutes.

Figure 2A:
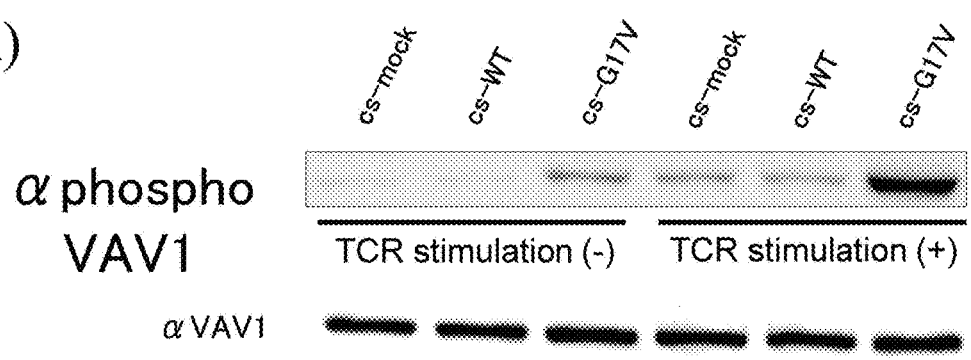
FIG. 2(A) indicates that in Jurkat cells, G17V RHOA mutant expression enhances Y174 phosphorylation which is indicative of VAV1 activation, and that this effect is enhanced upon anti-CD3 antibody stimulation.
Figure 2B:
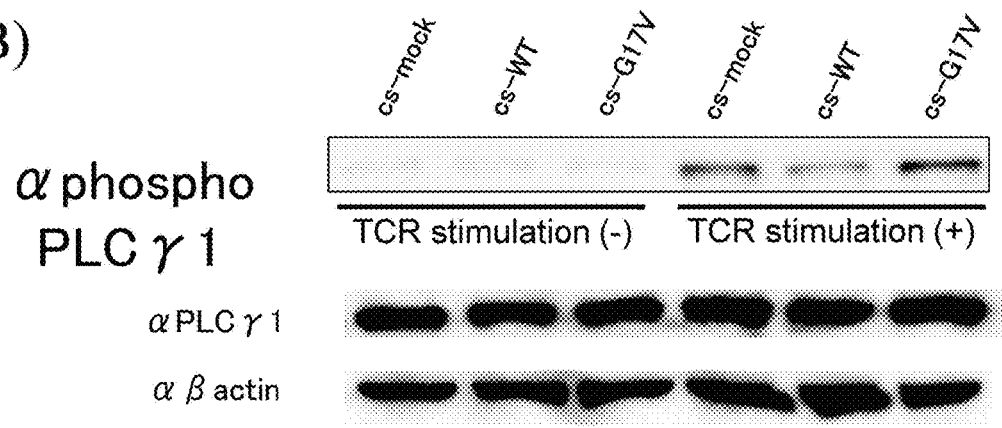
FIG. 2(B) indicates that in Jurkat cells, G17V RHOA mutant expression enhances phospholipase C (PLC)-gamma 1 phosphorylation under anti-CD3 antibody stimulation.

(3) After each of the procedures shown in (1) and (2) above, the samples were electrophoresed on an acrylamide gel and then blotted on Immobilon P (Promega), and then stained with anti-VAV1 antibody (Abcam or Cell signaling), anti-VAV1 Y174 antibody, anti-PLC-gamma 1 antibody (Cell signaling) or anti-phospho PLC-gamma 1 antibody (Cell signaling) as a primary antibody and HRP-labeled anti-rabbit IgG antibody (Dako) as a secondary antibody, or with anti-flag M2 antibody (Sigma) as a primary antibody and HRP-labeled anti-mouse IgG antibody (Dako) as a secondary antibody, followed by color development using Immobilon Western chemiluminescence HRP substrate (Millipore) and photography. The results obtained are shown in FIGS. 1 and 2.

Example 2

Figure 3:
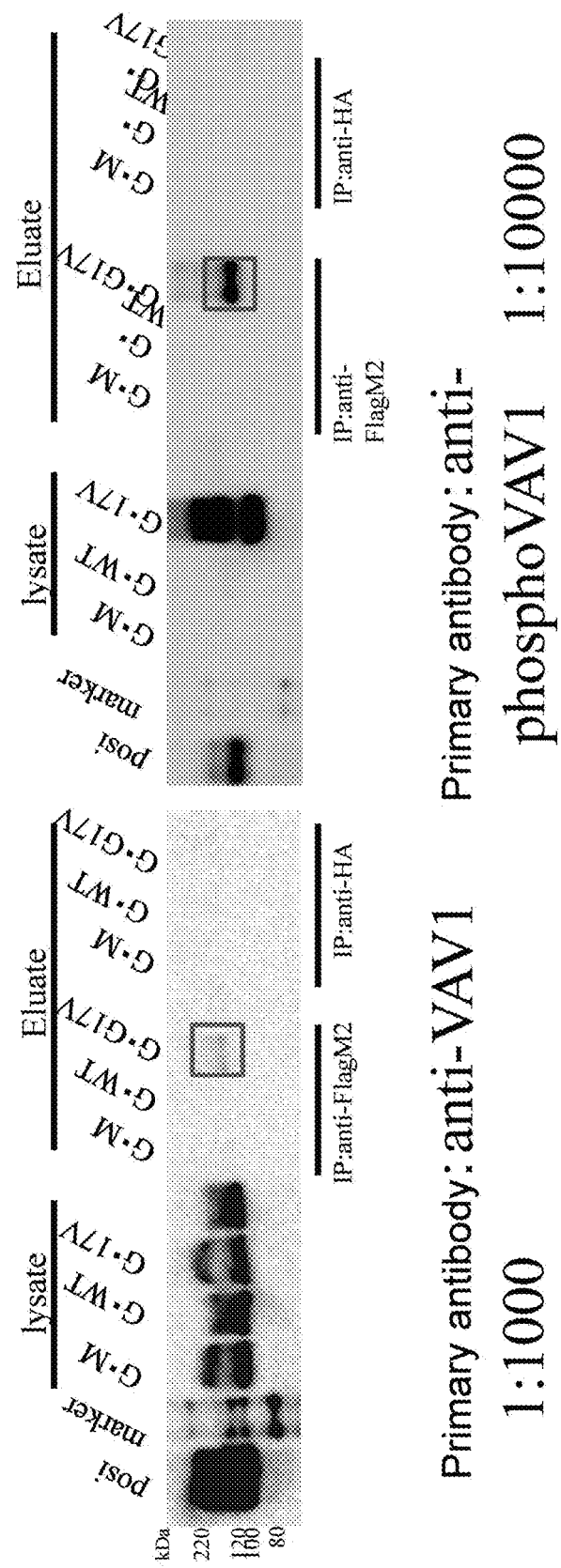
FIG. 3 indicates that in adult T-cell leukemia/lymphoma cell line SU9T01 cells, a G17V RHOA mutant binds to VAV1, which is a molecule important for T cell receptor (TCR) signaling.
Figure 4B:
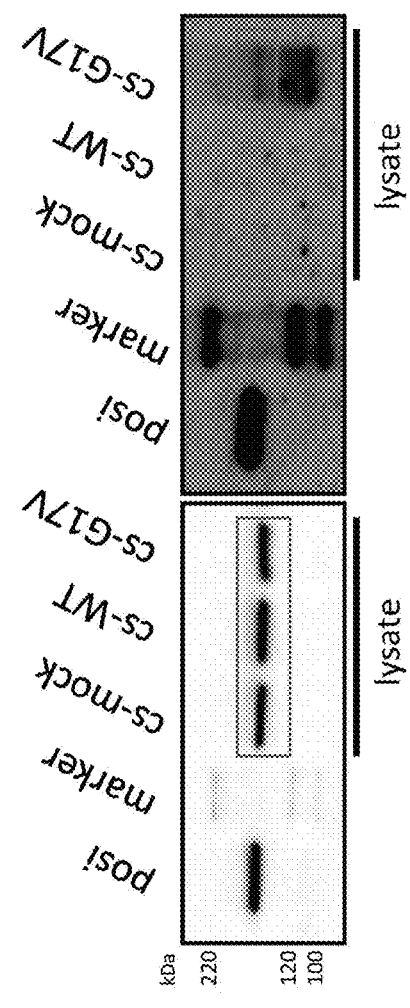
FIG. 4(B) indicates that in SU9T01 cells, G17V RHOA mutant expression enhances phospholipase C (PLC)-gamma 1 phosphorylation.
Figure 4A:
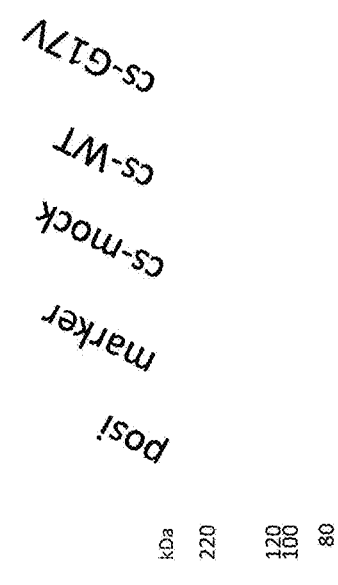
FIG. 4(A) indicates that in SU9T01 cells, G17V RHOA mutant expression enhances Y174 phosphorylation which is indicative of VAV1 activation.

SU9T01 cells (adult T-cell leukemia/lymphoma cell line) engineered with a lentivirus-mediated Tet-On system to express wild-type RHOA or G17V RHOA cDNA were seeded in RPMI (10% FCS, 1% PS) at $2 \times 10^5$ cells/mL in 15 cm petri dishes in triplicate. Doxycycline was added to give a final concentration of 2 µg/mL. On the following day, the cells were collected and then washed once with PBS. To the pellets, Lysis buffer was added in a volume of 1000 µl/tube. The same experiments as conducted on the Jurkat cells in Example 1 were then repeated. The results obtained are shown in FIGS. 3 and 4.

Example 3

In a 96-well flat-bottomed plate, LEAF™ purified anti-human CD3 Ab (BioLegend) adjusted to 10 µg/ml with sterile phosphate buffered saline (PBS) was dispensed in a volume of 50 µL/well and incubated overnight at 4'C. After removal of the antibody solution, each well was washed three times with sterile PBS.

Jurkat cells were seeded at $5 \times 10^4$ cells/well in a 24-well plate. On the following day, using X-tremeGENE HP DNA transfection reagent, the cells were transiently transfected with pGL4.30 vector designed to carry an NFAT response element and cDNA encoding firefly luciferase (Promega), phRL vector designed to carry cDNA encoding renilla luciferase (Promega) and pEF vector designed to carry wild-type or G17V RHOA cDNA. At 24 hours after transfection, the cultured cell suspensions were each dispensed in a volume of 150 µl/well.

After 7 hours, the cultured cell suspensions were collected into tubes, and PBS was further dispensed into the culture plate in a volume of 200 µl/well, followed by pipetting and collection into the tubes. This operation was repeated to completely collect the cells. The cells were washed once with PBS.

Figure 5:
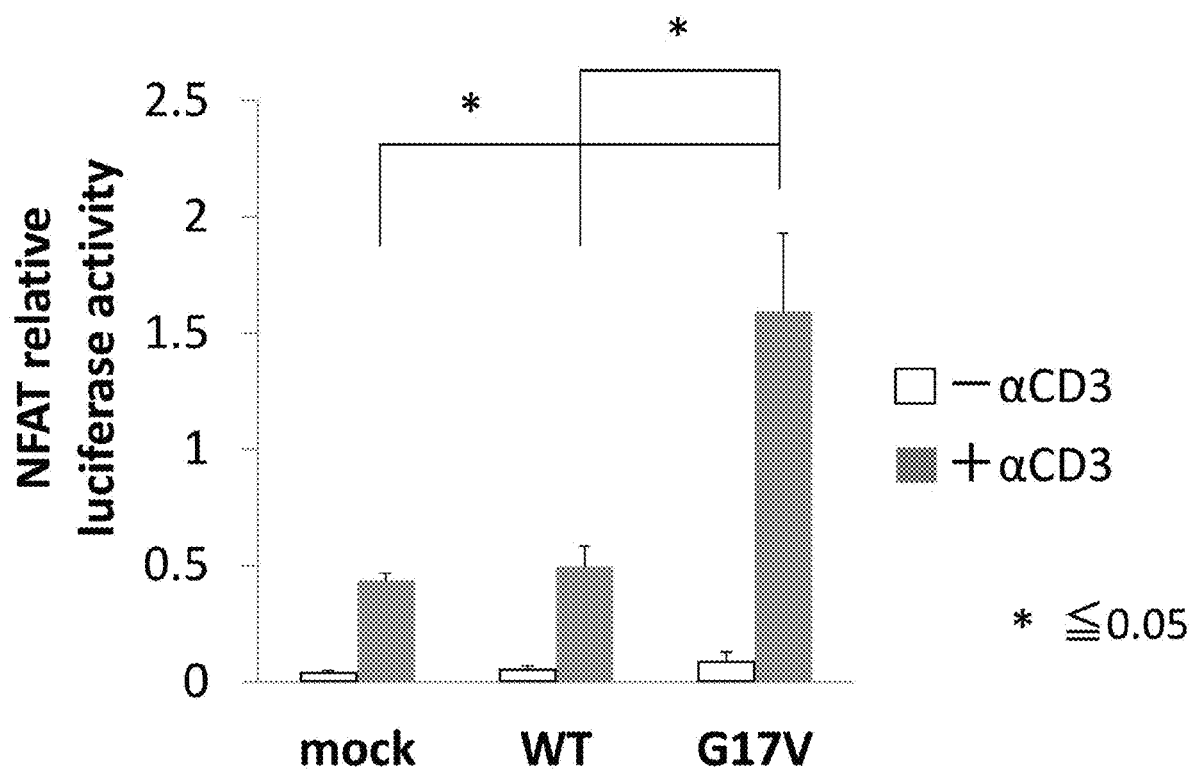
FIG. 5 indicates that in Jurkat cells, G17V RHOA mutant expression enhances NFAT (nuclear factor of activated T-cells) activity.

In accordance with the protocol of Dual Luciferase Reporter Assay (Promega), firefly luciferase activity and renilla luciferase activity were each measured, and the value of firefly luciferase was divided by the value of renilla luciferase to correct the transfection efficiency. In more detail, the cells were mixed with Passive Lysis Buffer (PLB) in a volume of 100 µl/tube, followed by freezing at −80° C. to lyse the cells. After centrifugation, the supernatants were collected. In a 96-well plate. LARII was dispensed in a volume of 100 µl/well. 20 µl of each cell lysate was added. The plate was mounted on a luminometer and Stop & Glo® Reagent was added in 100 µL volumes, followed by measurement again with the luminometer. The results obtained are shown in FIG. 5.

Example 4

Dynabeads T-activator CD3/CD28 (Veritas) were mixed with buffer (PBS supplemented with 0.1% BSA+2 mM EDTA, pH 7.4) and allowed to stand on a magnetic rack to remove the supernatant.

Jurkat cells engineered with a lentivirus-mediated Tet-On system to express wild-type or G17V RHOA cDNA were seeded in RPMI (10% FCS, 1% PS) at $2 \times 10^5$ cells/mL in 15 cm petri dishes in triplicate. Doxycycline was added to give a final concentration of 2 µg/mL. On the following day, the cells were collected and seeded in a 24-well plate. The Dynabeads T-activator CD3/CD28 (Veritas) washed above were added. After 3 and 6 hours, the cells were collected.

Figure 6:
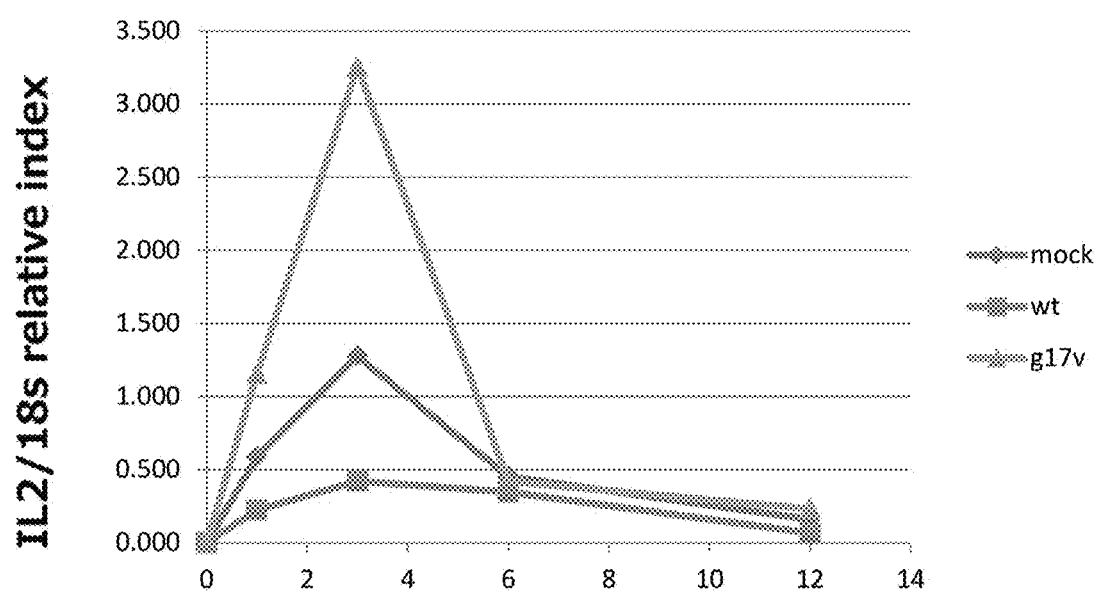
FIG. 6 indicates that in Jurkat cells, G17V RHOA mutant expression enhances interleukin-2 mRNA expression.

The cells were washed once with PBS and their RNA was extracted with an RNeasy Mini Kit (Qiagen). SuperscriptIII (Thermo Fisher Scientific) was used to synthesize cDNA. IL-2 mRNA was measured with the primer/probe sets of Taqman Gene Expression Assays (Thermo Fisher Scientific). rRNA was measured with TaqMan® Ribosomal RNA Control Reagents (Thermo Fisher Scientific) and used for correction. The results obtained are shown in FIG. 6.

2. Data Indicating that Dasatinib Cancels VAV1 Activation Induced by G17V RHOA Mutant and Downstream Signaling (Examples 5 and 6)

Example 5

Jurkat cells engineered with a lentivirus-mediated Tet-On system to express wild-type RHOA or G17V RHOA cDNA were seeded in RPMI (10% FCS, 1% PS) at $2\times10^5$ cells/mL in 15 cm petri dishes in triplicate. Doxycycline was added to give a final concentration of 2 µg/mL. On the following day, the cells were collected and centrifuged, and then seeded in RPMI (serum-free) at $6\times10^5$ cells/mL in 15 cm petri dishes in triplicate. After 3.5 hours, dasatinib was added at a final concentration of 0 to 10 nM. After 30 minutes, the cells were collected. The same experiments as conducted in Example 1 were then repeated. The results obtained are shown in FIG. 7.

Example 6

Figure 8:
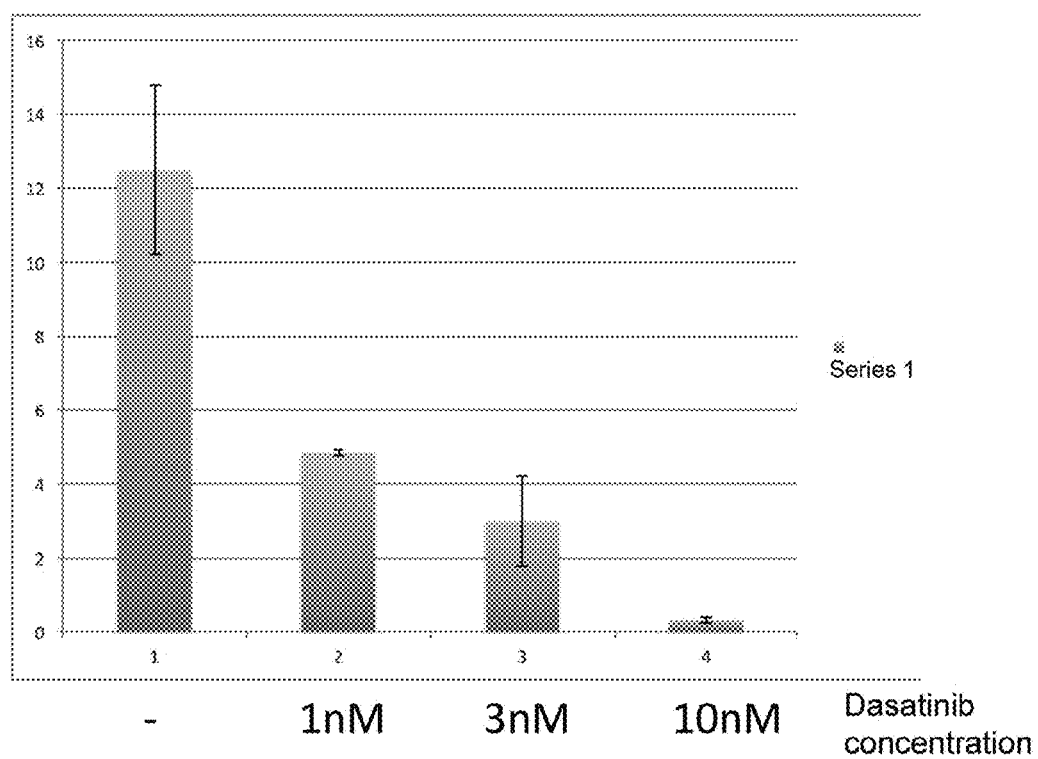
FIG. 8 indicates that in Jurkat cells, dasatinib cancels the enhanced interleukin-2 mRNA expression induced by G17V RHOA mutant expression.

Jurkat cells engineered with a lentivirus-mediated Tet-On system to express wild-type RHOA or G17V RHOA cDNA were seeded in RPMI (10% FCS, 1% PS) at $2\times10^5$ cells/mL in 15 cm petri dishes in triplicate. Doxycycline was added to give a final concentration of 2 µg/mL. On the following day, the cells were collected and seeded in a 24-well plate. Dasatinib was added at a final concentration of 0 to 10 nM. Dynabeads T-activator CD3/CD28 (Veritas) washed in the same manner as shown in Example 4 were added. After 3 hours, the cells were collected. The cells were washed once with PBS and their RNA was extracted with an RNeasy Mini Kit (Qiagen). SuperscriptIII (Thermo Fisher Scientific) was used to synthesize cDNA. IL-2 mRNA was measured with the primer/probe sets of Taqman Gene Expression Assays (Thermo Fisher Scientific). rRNA was measured with TaqMan® Ribosomal RNA Control Reagents (Thermo Fisher Scientific) and used for correction. The results obtained are shown in FIG. 8.

3. Discovery of VAV1 Gene Mutations by Genomic Analysis (Examples 7 t 11.)

Example 7

Figure 9:
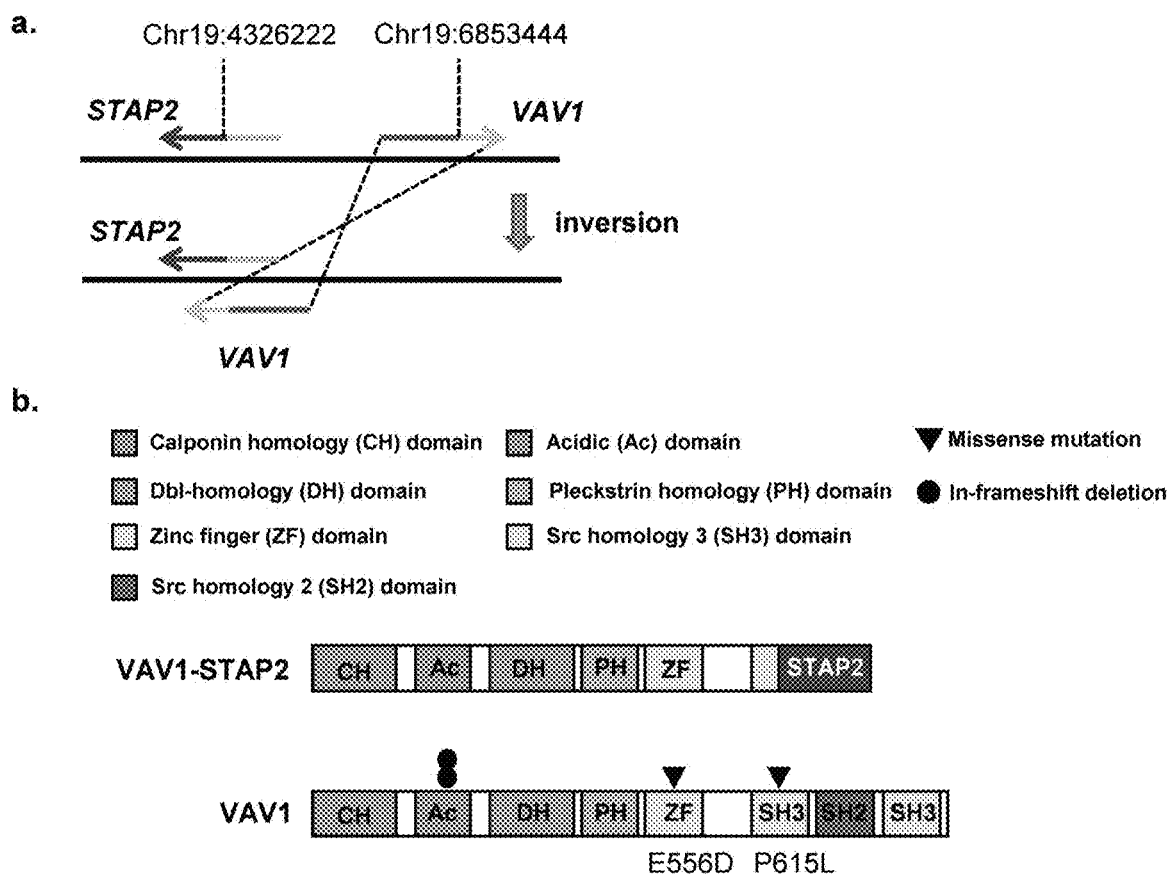
FIG. 9 indicates that there are VAV1 gene mutations in AITL and peripheral T-cell lymphoma, not otherwise specified.

A library was prepared using an AmliSeq system (Thermo Fisher Scientific) for regions comprising exons of the VAV1 gene or prepared using an Ion Plus Fragment Library kit (Thermo Fisher Scientific) for PCR amplicons amplified by genomic PCR using KOD Plus neo (TOYOBO). After sequencing was conducted with an Ion Torrent PGM sequencer (Thermo Fisher Scientific) in accordance with a standard protocol for 300 base pairs, mutation candidates were analyzed by Variant caller software and their results were confirmed by direct sequencing. The results obtained are shown in FIG. 9.

Example 8

Figure 10:
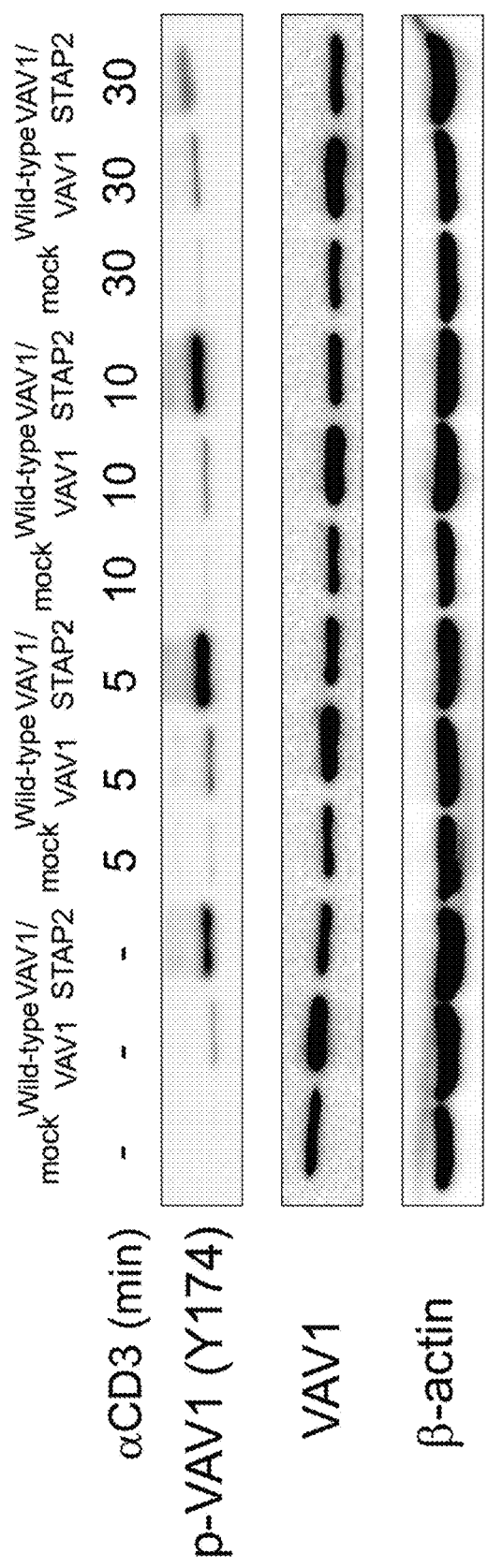
FIG. 10 indicates that in Jurkat cells, VAV1 mutant expression enhances Y174 phosphorylation.
Figure 11:
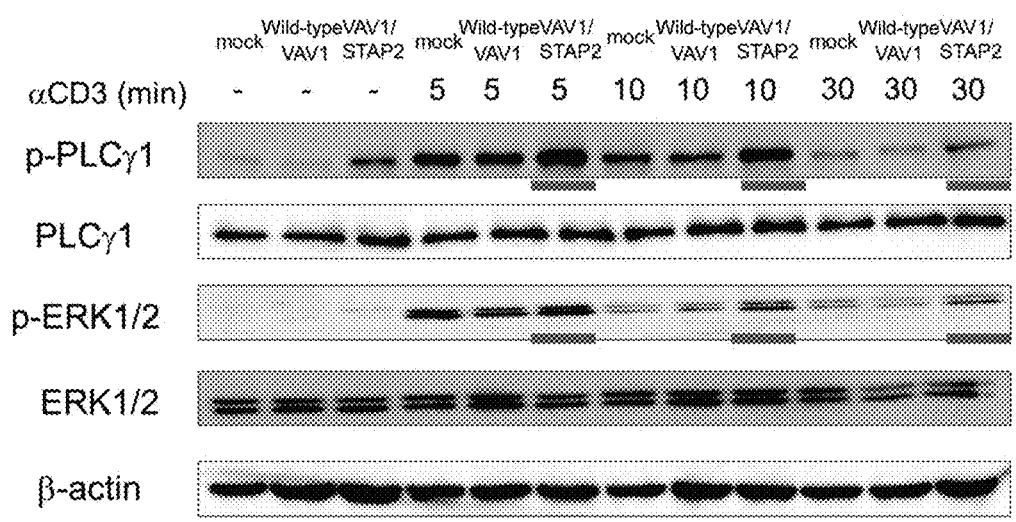
FIG. 11 indicates that in Jurkat cells, VAV1 mutant expression enhances PLC-gamma 1 phosphorylation.

Jurkat cells engineered with a lentivirus-mediated Tet-On system to express wild-type VAV1 or VAV-STAP2 cDNA were seeded in RPMI (10% FCS, 1% PS) at $2\times10^5$ cells/mL in 15 cm petri dishes in triplicate. Doxycycline was added to give a final concentration of 2 µg/mL. The same experiments as conducted on the Jurkat cells engineered to express wild-type or G17V RHOA cDNA were then repeated by reference to Example 1, etc. The results obtained are shown in FIGS. 10 and 11.

Example 9

Figure 12:
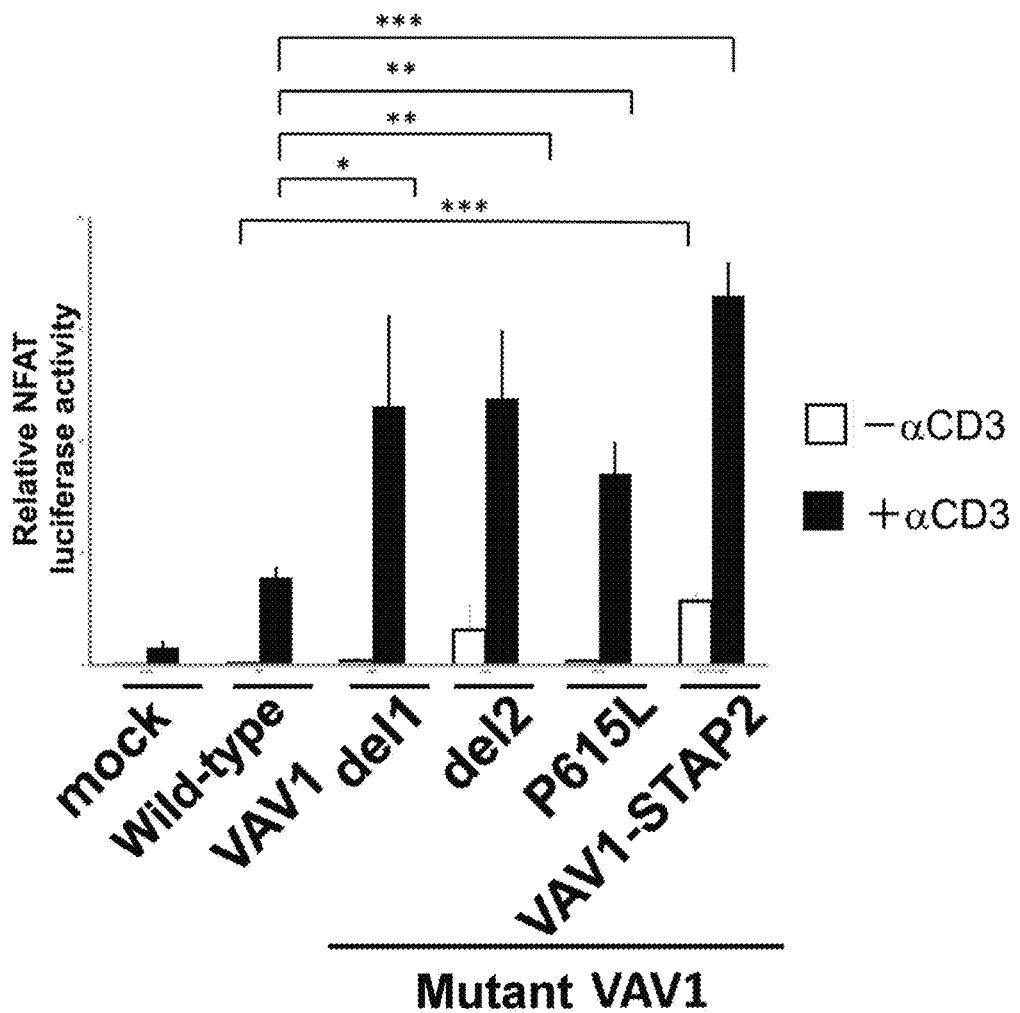
FIG. 12 indicates that in Jurkat cells, VAV1 mutant expression enhances NFAT activity.

Using X-tremeGENE HP DNA transfection reagent, Jurkat cells were transfected with pGL4.30 vector designed to carry an NFAT response element and cDNA encoding firefly luciferase (Promega), phRL vector designed to carry cDNA encoding renilla luciferase (Promega) and pEF vector designed to carry wild-type or mutant VAV cDNA. The cells were then stimulated with LEAF™ purified anti-human CD3 Ab (BioLegend) and measured for firefly luciferase activity and renilla luciferase activity, as in the case of wild-type or G17V RHOA cDNA, by reference to Example 3, etc. The results obtained are shown in FIG. 12.

Example 10

In a 24-well flat-bottomed plate, LEAF™ purified anti-human CD3 Ab (BioLegend) adjusted to 10 gig/ml with PBS was dispensed in a volume of 200 µL/well and incubated overnight at 4° C. After removal of the antibody solution, each well was washed three times with sterile PBS.

Figure 13:
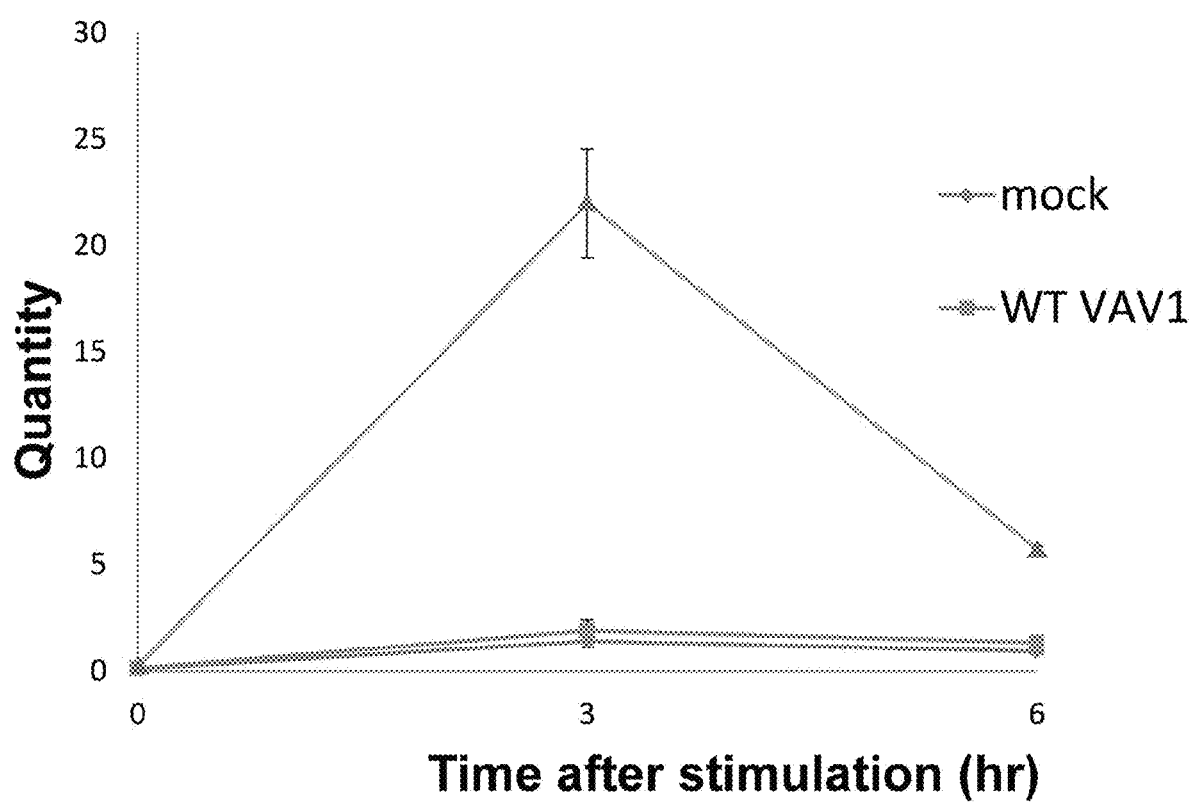
FIG. 13 indicates that in Jurkat cells. VAV1 mutant expression enhances interleukin-2 mRNA expression.

Jurkat cells engineered with a lentivirus-mediated Tet-On system to express wild-type VAV1 or various mutant VAV cDNAs were seeded. After 3 and 6 hours, the cells were collected, and the same experiments as in the case of wild-type or G17V RHOA were repeated by reference to Example 4, etc. The results obtained are shown in FIG. 13.

Example 11

Figure 14:
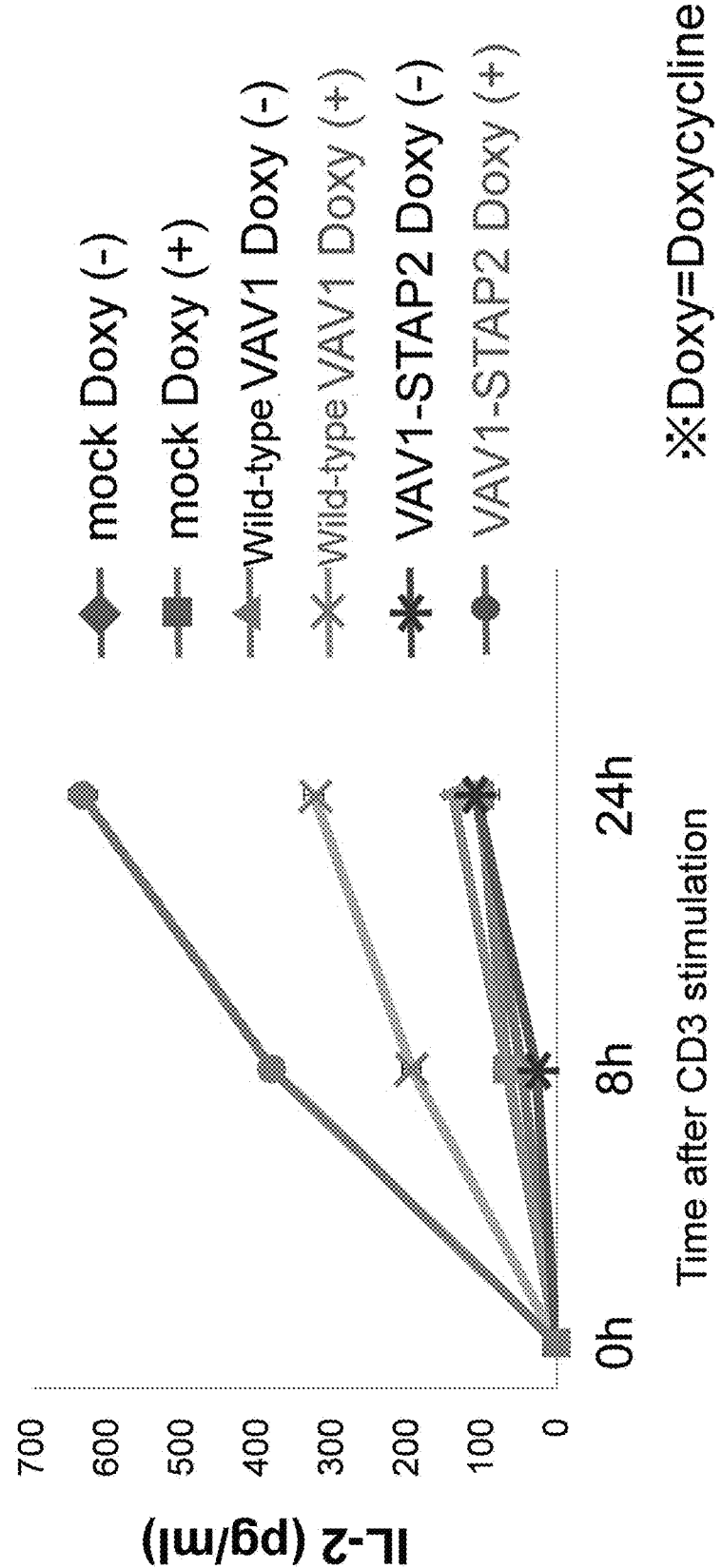
FIG. 14 indicates that in Jurkat cells, VAV1 mutant expression enhances interleukin-2 secretion into the supernatant.

Jurkat cells engineered with a lentivirus-mediated Tet-On system to express wild-type VAV1 or VAV-STAP2 cDNA were seeded in a 24-well plate at $5\times10^4$ cells/well in a volume of 500 µl/well. Doxycycline (2 µg/ml) was added and the cells were collected after 24 hours, and the cell suspensions were each dispensed at $5\times10^4$ cells/50 µl/well in a 96-well plate which had been coated with LEAF™ purified anti-human CD3 Ab (BioLegend) in the same manner as shown in Example 3 above. At 0, 8 and 24 hours after stimulation, the culture supernatants were collected. IL-2 was measured using a BD) cytometric beads array. The results obtained are shown in FIG. 14.

4. Dasatinib-Induced Inhibition of VAV1 Mutation Activation Examples 12 and 13)

Example 12

Figure 15:
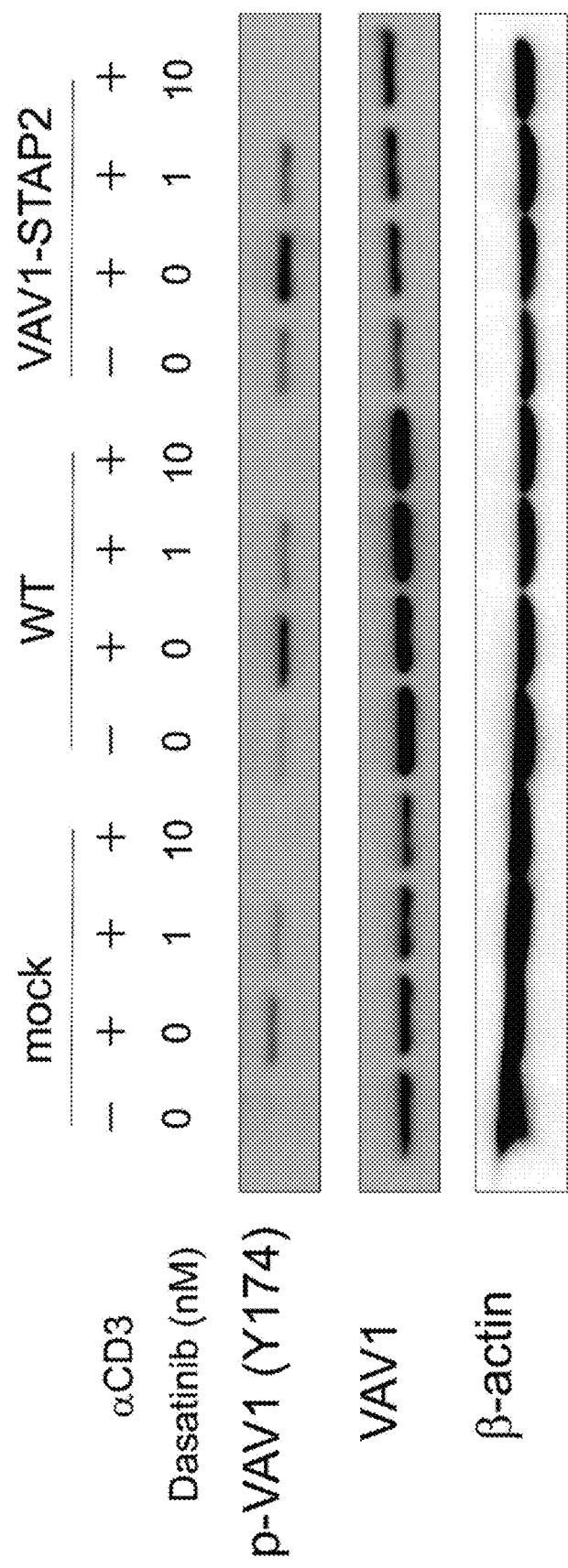
FIG. 15 indicates that in Jurkat cells, dasatinib cancels the enhanced Y174 phosphorylation induced by VAV1 mutant expression.

Jurkat cells engineered with a lentivirus-mediated Tet-On system to express wild-type VAV1 or VAV1-STPA2G cDNA were seeded in RPMI (10% FCS, 1% PS) at $2\times10^5$ cells/mL in 15 cm petri dishes in triplicate. Doxycycline was added to give a final concentration of 2 µg/mL. On the following day, the cells were collected and centrifuged, and then seeded in RPMI (serum-free) at $6\times10^5$ cells/mL in 15 cm petri dishes in triplicate. After 3.5 hours, dasatinib was added at a final concentration of 0 to 10 nM. After 30 minutes, the cells were collected. The same procedures as shown above were then repeated to conduct a stimulation experiment with anti-CD3 antibody. The results obtained are shown in FIG. 15.

Example 13

In a 96-well flat-bottomed plate, LEAF™ purified anti-human CD3 Ab (BioLegend) adjusted to 10 μg/ml with PBS was dispensed in a volume of 50 μL/well and incubated overnight at 4° C. After removal of the antibody solution, each well was washed three times with sterile PBS.

Figure 16:
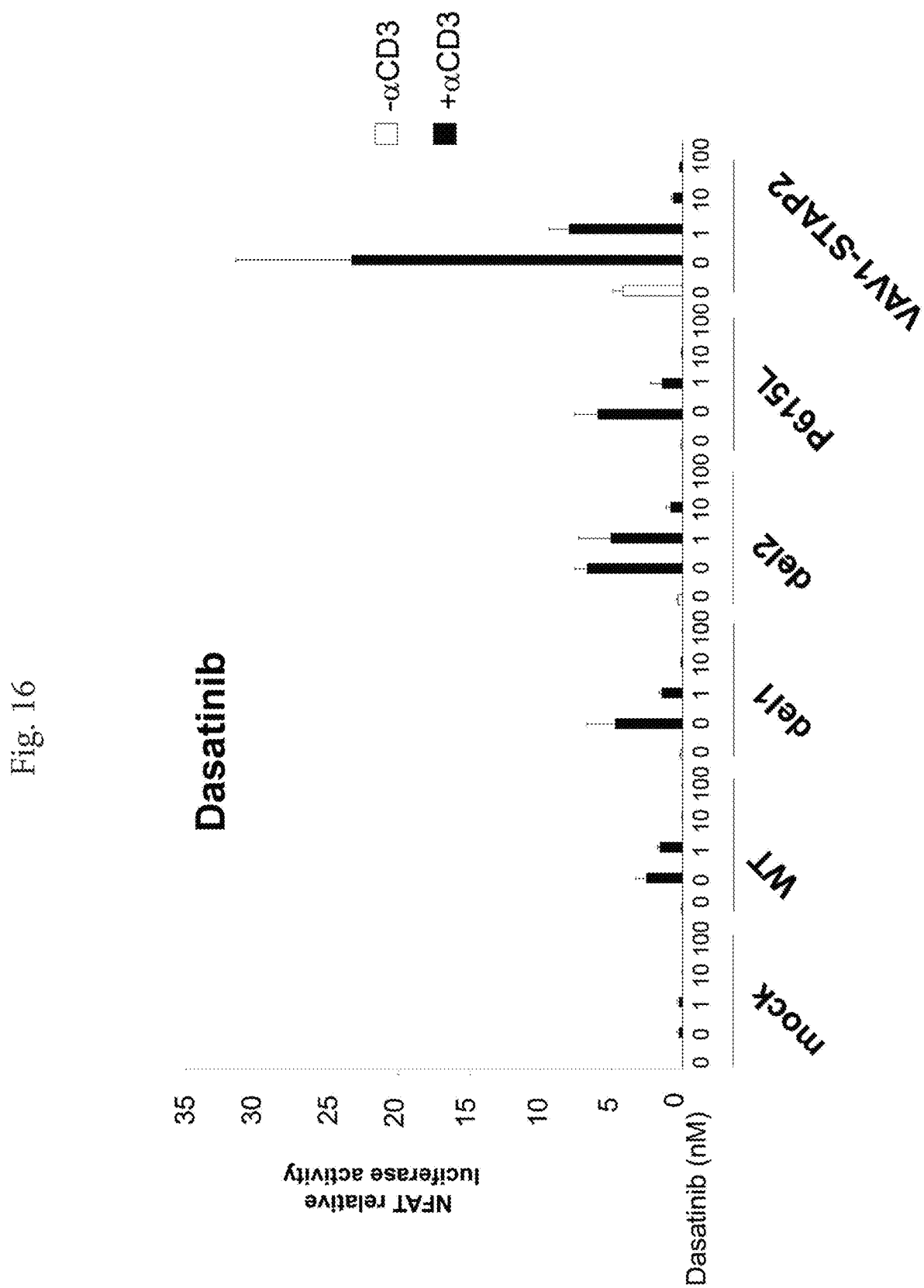
FIG. 16 indicates that in Jurkat cells, dasatinib cancels the enhanced NFAT activity induced by VAV1 mutant expression.

Jurkat cells were seeded at $5 \times 10^4$ cells/well in a 24-well plate. On the following day, using X-tremeGENE HP DNA transfection reagent, the cells were transiently transfected with pGL4.30 vector designed to carry an NFAT response element and cDNA encoding firefly luciferase (Promega), phRL vector designed to carry cDNA encoding renilla luciferase (Promega) and pEF vector designed to carry wild-type or G17V RHOA cDNA. At 24 hours after transfection, dasatinib was added at a final concentration of 0 to 10 nM. After 30 minutes, the cells were collected and then stimulated with LEAF™ purified anti-human CD3 Ab (BioLegend) and measured for firefly luciferase activity and renilla luciferase activity by reference to Example 3 described above, etc. The results obtained are shown in FIG. 16.
5. Tumor Suppressive Effect Upon Administration of Dasatinib to Therapeutic Model Mice (Example 14)

Example 14

(1) Preparation of Model Mice

80% or more of angioimmunoblastic T-cell lymphoma (AITL) cases show loss-of-function mutations in the TET2 gene, and a G17V RHOA gene mutation is also found in about 70% of all cases. To prepare an animal model of this disease, the following genetically modified mice were prepared.

Mice were genetically modified as follows at the fertilized egg stage.

i) Fertilized eggs are engineered to have a lox sequence inserted into the Tet2 gene, whereby mice are designed to disrupt the Tet2 gene by the action of Cre recombinase.

ii) Fertilized eggs are engineered to have a DNA sequence (Cre expression cassette) composed of Cre recombinase ligated downstream of the Mx promoter. In cells responsive to interferon, the Mx promoter is activated upon interferon stimulation to thereby cause the expression of Cre recombinase. For this reason, upon administration of poly-inosilic:poly-cytidilic acid (pIpC) capable of inducing interferon production, Cre recombinase is expressed in these cells responsive to interferon (which also include hematopoietic stem cells). Namely, i) and ii) mean that mice are designed such that the Tet2 gene is disrupted and inactivated in hematopoietic stem cells upon pIpC administration.

iii) Independently of i) and ii) above, fertilized eggs are engineered to have a DNA sequence (expression cassette) composed of G17V mutant human RHOA cDNA ligated downstream of the CD2 promoter. Since the CD2 promoter is specifically activated in T cells, a G17V mutant RHOA protein is expressed only in T cells.

When the thus prepared mice were intraperitoneally administered four times with 20 mg/kg pIpC every two days starting from 4 weeks of postnatal age, multiple lymph node swelling and splenomegaly were observed in many mice at about 40 weeks of age to 50 weeks of age, and these mice died at 45 weeks of age or later. For detailed analysis, mice showing splenomegaly or hyposthenia at 35 weeks of age or later were sacrificed for further analysis. Histological observation of swollen lymph nodes and spleens showed not only 10% to 30% infiltration of T cells regarded as tumor cells, but also infiltration of lymphocytes and other various inflammatory cells, thus resulting in a pathological image where tumor and inflammation were difficult to distinguish from each other. T cells growing in a tumor-like fashion were found to have characteristics of follicular helper T cells, as seen from their expression pattern of cell surface antigens. When DNA was prepared from swollen lymph nodes to analyze T cell receptor reconstitution, it was indicated that T cell receptor reconstitution was mono- or oligo-clonal, thus yielding the results that were not inconsistent with the tumor-like growth of T cells. Moreover, some of the mice also showed tumor formation in their liver, lungs and other organs, so that tumor-like infiltration of lymphocyte-like cells was observed histologically.

In AITL patients, tumor cells are known to have characteristics of follicular helper T cells. Moreover, the ratio of tumor cells in their tumor tissue is low, and the great majority of cells are various kinds of inflammatory cells in most cases. AITL patients cannot be pathologically diagnosed as having tumor and are therefore often diagnosed as having inflammation. Thus, the disease occurring in the mice in this example has the same characteristics as seen in AITL patients. (This mouse model is not regarded as a perfect model of AITL, but there has been no report showing that tumor having such characteristics was modeled in mice; and hence there is no doubt that this model is most similar to AITL patients.)
(2) Transplant Model An AITL model is regarded as having been established, but a long incubation period is required to observe oncogenesis after pIpC administration. For this reason, this genetically modified mouse model is not suitable for use in therapeutic experiments. Thus, an attempt was made to establish a transplant model. When all cells prepared from swollen lymph nodes were allowed to float and then intraperitoneally transplanted into many nude mice, lymph node swelling was observed in almost all of the host mice within about one month. Their histological study showed that their swollen lymph nodes were substantially the same as those in the mouse used as a donor, while their cytological study also showed an increase in T cells having characteristics of follicular helper T cells. It should be noted that inflammatory cells migrating to the tumor tissue were composed of donor mouse-derived cells and host mouse-derived cells in admixture.

Figure 17:
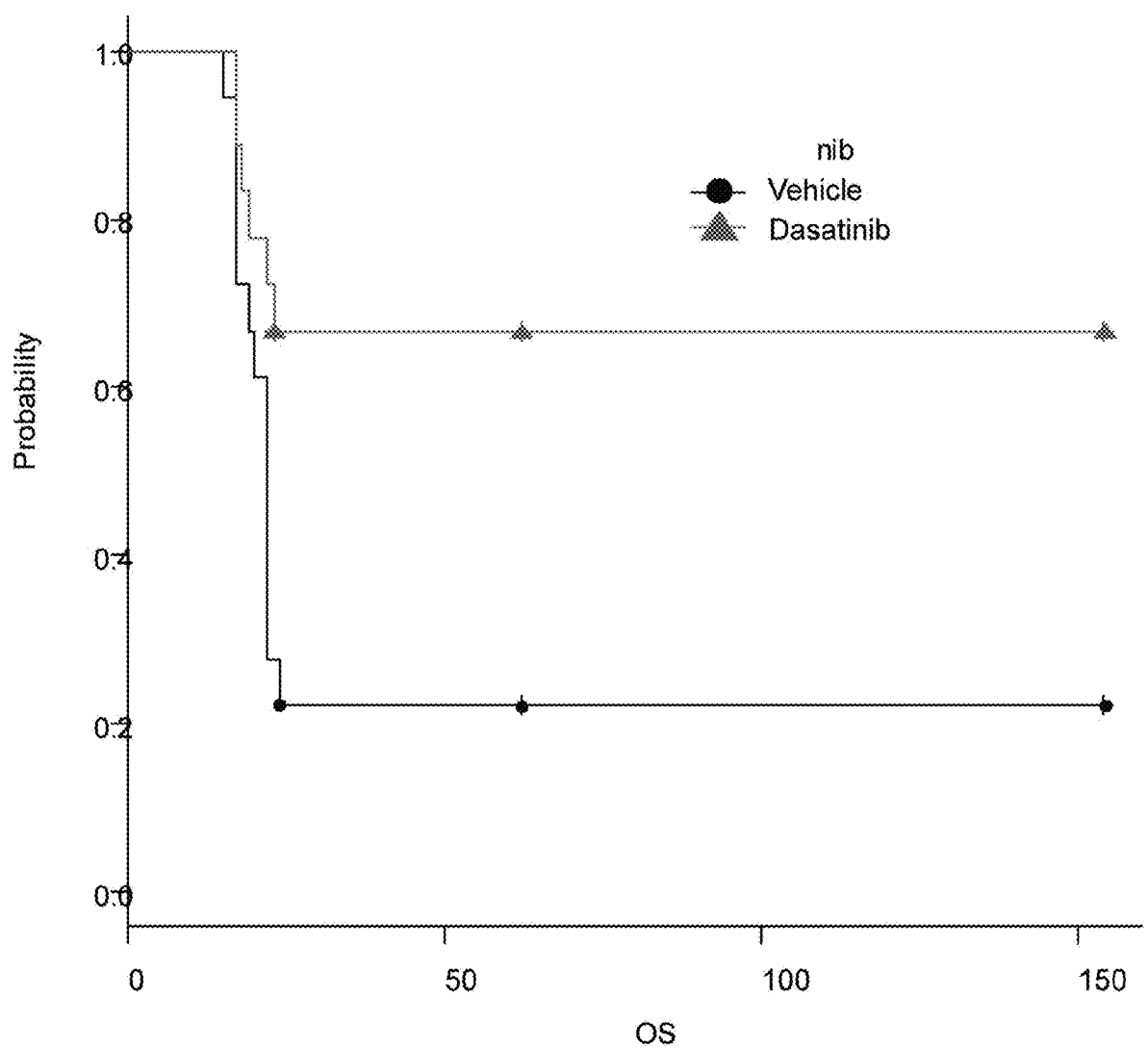
FIG. 17 is a graph comparing the survival rate ("Probability" in the figure) between groups where nude mice (AITL model mice) were intraperitoneally injected with donor mouse swollen lymph node-derived cells and then administered with dasatinib (the dasatinib group: "Dasatinib" in the figure) and not administered with dasatinib (the control group: "Vehicle" in the figure).

On the other hand, even when only cells having characteristics of follicular helper T cells (i.e., $CD4^+$ $ICOS^+$ cells) were isolated from swollen lymph node cells of the donor mouse and provided for transplantation into nude mice, lymphoma did not occur (*).
(3) Therapeutic Model Donor mouse swollen lymph node-derived cells ($2 \times 10^7$ cells) were all intraperitoneally injected into nude mice and, after 2 weeks (after lymph node swelling was observed by echography in some mice), 5 mg/kg of dasatinib dissolved in a solution of propylene glycol:distill water adjusted to 1:1 was orally administered to the mice for successive 14 days (the dasatinib group: "Dasatinib" in FIG. 17). As a control, nude mice under completely the same conditions were administered with the same volume of the solution alone (propylene glycol: distill water=1:1) according to the same schedule (the control group: "Vehicle" in FIG. 17). The results of these administration experiments are show in FIG. 17. In the control group, 77.8% ($^{14}/_{18}$) of the mice showed progression of lymphoma (body weight loss and hypostenia) at 20 days, whereas in the dasatinib group, only 33.3% (6/18) of the mice showed progression of lymphoma during the observation period of 150 days, so that progression was significantly suppressed and survival was prolonged in the dasatinib group.

In addition, donor mouse swollen lymph node-derived cells ($2 \times 10^7$ cells) were all intraperitoneal injected into nude mice and, after 2 weeks, dasatinib or a control solution was administered three times daily for 2 days in accordance with the above procedure. On the following day, the nude mice were sacrificed, and thin section specimens were prepared from their swollen lymph nodes and then stained with anti-phosphorylated VAV1 antibody. As a result, phosphorylated VAV1 was stained in swollen lymph nodes from the mice of the group receiving the control solution, whereas phosphorylated VAV1 was not stained in swollen lymph nodes from the mice of the group receiving dasatinib (this result supports the hypothesis that the tumor suppressive effect of dasatinib is mediated by VAV1 phosphorylation suppression).

(4) Contribution of Microenvironmental Cells to AITL Development

As seen from the description indicated with * in (2) above, even when only cells having characteristics of follicular helper T cells (i.e., CD4 ICOS cells) were isolated from swollen lymph node cells of the donor mouse and provided for transplantation into nude mice, lymphoma did not occur. However, this suggests that donor-derived microenvironmental cells contribute to AITL development.

Simultaneously with the preparation of model mice in (1) above, mice differing from these model mice only in ii) below were also prepared.

i) Fertilized eggs are engineered to have a lox sequence inserted into the Tet2 gene, whereby mice are designed to disrupt the Tet2 gene by the action of Cre recombinase (completely the same as in the case of the model mice in (1) above).

ii) Fertilized eggs are engineered to have a DNA sequence (Cre expression cassette) composed of Cre recombinase ligated downstream of the CD4 promoter. The CD4 promoter used here is known to be activated primarily in T cells and to induce the downstream gene expression. Namely, i) and ii) mean that mice are designed such that the Tet2 gene is disrupted and inactivated in T cells.

iii) Independently of i) and ii) above, fertilized eggs are engineered to have a DNA sequence (expression cassette) composed of G17V mutant human RHOA cDNA ligated downstream of the CD2 promoter. Since the CD2 promoter is specifically activated in T cells, a G17V mutant RHOA protein is expressed only in T cells (completely the same as in the case of the model mice in (1) above).

In this mouse model, lymph node swelling was not observed at all until 80 weeks of age. Taken together with the description indicated with * in (2) above, this result was deemed to strongly suggest that Tet2 inactivation was required to occur in inflammatory cells other than T cells, and these Tet2-inactivated inflammatory cells would contribute to oncogenesis in tissue.

The invention claimed is:

1. A method for treating a tumor in a subject in need thereof, the method comprising
administering dasatinib or a prodrug thereof or a pharmacologically acceptable salt thereof or a hydrate or solvate thereof to the subject having the tumor, wherein the tumor comprises
a phosphorylated proto-oncogene protein belonging to a VAV family or
a gene mutation or gene fusion in a RHOA gene or in the phosphorylated proto-oncogene belonging to the VAV family.

2. The method according to claim 1, wherein the proto-oncogene protein is a VAV1 protein.

3. The method according to claim 1, wherein the tumor is selected from the group consisting of T-cell lymphoma, gastric cancer, pancreatic cancer, skin tumor, colorectal cancer, uterine cancer and nervous system tumor.

4. The method according to claim 1, wherein the tumor is a T-cell lymphoma.

5. The method according to claim 4, wherein the T-cell lymphoma is an angioimmunoblastic T-cell lymphoma or a peripheral T-cell lymphoma.

6. The method according to claim 1, wherein the tumor comprises the phosphorylated proto-oncogene protein belonging to the VAV family.

7. The method according to claim 1, wherein the tumor comprises the gene mutation or gene fusion in the RHOA gene or in the phosphorylated proto-oncogene belonging to the VAV family.

8. The method according to claim 7, wherein the tumor comprises the gene mutation in the RHOA gene.

9. The method according to claim 8, wherein the gene mutation is a glycine to valine substitution at amino acid position 17 of a RHOA protein encoded by the RHOA gene.

* * * * *